(12) United States Patent
Rothstein

(10) Patent No.: US 7,723,505 B2
(45) Date of Patent: May 25, 2010

(54) EAAT2 PROMOTER AND USES THEREOF

(75) Inventor: Jeffrey D. Rothstein, Catonsville, MD (US)

(73) Assignee: The John Hopkins University, Baltimore, MD (US)

( * ) Notice: Subject to any disclaimer, the term of this patent is extended or adjusted under 35 U.S.C. 154(b) by 843 days.

(21) Appl. No.: 10/480,179

(22) PCT Filed: Feb. 14, 2003

(86) PCT No.: PCT/US03/04414

§ 371 (c)(1),
(2), (4) Date: Dec. 8, 2003

(87) PCT Pub. No.: WO03/070965

PCT Pub. Date: Aug. 28, 2003

(65) Prior Publication Data

US 2005/0048488 A1      Mar. 3, 2005

Related U.S. Application Data

(60) Provisional application No. 60/357,179, filed on Feb. 15, 2002.

(51) Int. Cl.
C07H 21/04       (2006.01)
C07H 21/02       (2006.01)
C12N 5/00        (2006.01)
C12N 5/02        (2006.01)

(52) U.S. Cl. .................. 536/24.1; 536/23.1; 435/325

(58) Field of Classification Search .............. 536/24.1
See application file for complete search history.

(56) References Cited

U.S. PATENT DOCUMENTS 5,658,782 A     8/1997  Amara et al. ............... 435/365
2004/0166490 A1  8/2004  Morris et al. .................. 435/6
2004/0171108 A1  9/2004  Fisher et al. ............... 435/69.1

FOREIGN PATENT DOCUMENTS

WO     WO 99/47692         9/1999

OTHER PUBLICATIONS

AC090625, entered Jan. 9, 2002.*
AL133389, entered Jan. 31, 2002.*
Evans et al. nucleic acid sequence, Genbank accession No. B06133, submitted Jun. 26, 1996.*
Beato (FASEB J. vol. 5, pp. 2044-2051, 1991).*
Grimes et al (Molecular Biology Reports, vol. 24, pp. 175-184, 1997).*
Su ZZ, Leszczyniecka M, Kang DC, Sarkar D, Chao W, Volsky DJ, Fisher PB. Insights into glutamate transport regulation in human astrocytes: cloning of the promoter for excitatory amino acid transporter 2 (EAAT2). Proc Natl Acad Sci U S A. Feb 18, 2003;100(4):1955-60. Epub Feb 10, 2003.
Database GenCore, AN AC090625, Birren, B. et al. 'Homo sapiens Chromosome 11, clone RP3-683L5'. Gene Sequence, Jan. 9, 2002.

* cited by examiner

*Primary Examiner*—Valarie Bertoglio
(74) *Attorney, Agent, or Firm*—Edwards Angell Palmer & Dodge LLP; Peter F. Corless; Jonathan M. Sparks

(57) ABSTRACT

The present invention provides nucleic acid molecules comprising the EAAT2 promoter, as well as screening assays useful for identifying compounds which modulate the activity of the EAAT2 promoter, and methods of treating neurological disorders comprising administration of EAAT2 promoter modulators.

18 Claims, 9 Drawing Sheets

FIG. 1A

| FIG. 1A-1 |
| FIG. 1A-2 |
| FIG. 1A-3 |

FIG. 1A-1

```
   1 AAAACCACCAGGGTTGTTGCTGGAAAGTTTTTATTCCTGGATTAAAGGCA
  51 AGGATCAGCCTGTATTTAGCAATTTCTTTTTTAAGGTTAATGTCCCATGC
 101 GCCACTTACTTCTGGGGCCCTGTTCCAACTCTGCTGCGCAGTGGACTCCCC
 151 TTCTAGGTCCAGCACTTCCCAACTCTGCTGCGCAGTGGACTCAATCCCCT
 201 GGGAAGTCCTTAAAAATGCCCAAGTCAGCCCCCGCCTACCCGCCAAAGAT
 251 GCATGGACCAGAAATCTCTGAAAGGTGGCCTGAGTATTACTATTTTCTAA
 301 AAGGCTCTCCAGACCATTTTAATGGGACACCCAGTGTTGAAAATAACTGC
 351 TCCAGTTTGTTAAAAAATAATTGGTGTGAATATTGGCAAAAGCCCTCTGG
 401 CACAAAGAAGAGAACCAGTTTCTTCTAGCTAATGTTGTTAGCCTTAGCCTCTGG
 451 TATCTGTGGCATAGTCCATGTGACTTAATAGACCTGGTCTTCCAGGGCAG
 501 CTGAATGCAAATGTTTCTCACGTGTAGAACGGATGTCAGGGCTTACAGA
 551 GAAAGTGGGAAACTGGAATGATGACTCCATCTAATTCGGCCATGCTGGAT
 601 GATTCACCTGGATTCTCTCATGTCCTGAGCATTGAAAACAACTCCATCCCTTTTCT
 651 TTTTTAAATTGAATGTTTAAAGAGTGAAAACAACTCCATCCCTTTTCT
 701 GTTTCCTTTACCTTGTATTTATGTACCACCAGGTACCTTGCTCTTGGCA
 751 GTGAGCGTGAATGGCACAGCTCAGCCTCTGAAGCCTGTGTGTGCAGAG
 801 ATTGAGGATTGTGATGAGTAGTCCATGTCATGCTCATGTTAAGGGGGGT
 851 GCTAATAGCAGACTAGTGCTCCTGCGATTATTAATATCTAGGTCTGGGAC
 901 AGATTGTGATGGCTTCTTTGTAAAGTTAGACAATTAGACTGTAAAGTTTGTATAT
 951 GAAACCCTAACTTGTAAACACAAAGACACACACTTACCCTTGACGGGCTTAAG
1001 GTGACAACTTCAGATACAAAGATATACCAAAGTGAAAGAAGATAGCTCTTCATCT
1051 AGGAGAGTGTCAAACATAAACACATTACCAGGTTAAACAATAACTAATTTTTC
1101 ACAAATTATTTTAAACACATTACCAGGTTAAACAATAACTAATTTTTC
1151 GGAAGAGAAGAGTACCCAAAGTCAAATGCCCTAAGACGAAGAGATGCTTA
```

```
1201  TGGCATTTTTTTTAAATAAAGAAAAATGCAAAGTTAGAGAGTGGTTCTGAAG
1251  GAACCTAGGATGAATAAGGTACAGACATGATTATTCTAATGGTGCAGACA
1301  GGATTGAGAGAAGGGGAGGGGAGAGATGGAGAAAGGCATGGATGGA
1351  AGATGACGTTTGGATTCAGATTTTAAATTTTATTAATGTGTTTCCCCTCTTTTTC
1401  AGCAGAGATTTATTTTTCTCATCTGTCTGTTCATACTTGGATATTTTGTCCAATAA
1451  TTGTTATTTTTCTCATCTGTCTGTTCATACTTGGATATTTTGTCCAATAA
1501  ACTATCTTCTAAGGACTCTGAAAATGCACTGAATATTTTTGGAGGTTTA
1551  CTGGGGTGCCAGACGCCACTTTAGGAGTTTTACATATCCTCTCCATTTCA
1601  TTTAGTTCTCTTAGCACAGAGAAGTGGGAGAAGATAGTCCCATTTTACAG
1651  GTGGGATGAAGAGAGAGATGGAGAATTTGCCCCAGGTTACTCAGCTAGA
1701  AGGTGGGTGAAGAACTCAAGCCTTCGGATATCAGCGCCTGGCATTTAACTA
1751  CCAATCGGTCCTCGCTGGGACTCCGGCTCCTCTGCACCATCCCCGGACC
1801  TACTCAGAGAGTTTGCACGTGGCCGTGCCGTTCCATCGTCTAACAAGT
1851  CCAGCACACAGCGCAAATCCGAAGATCGTCTACCCCGGGAAAAAGAGAGTC
1901  TGTTTAATTCTCCTGTGGCCCCTCCAAGTGAGTTCTTTTGGGTTCCATTGC
1951  CTAGACGAGGAAAGTGAGGCTTTGCCTGCTCTTGCGCTCACAGGGTCGGCA
2001  AGTAGTGGGACCCTAGGTTCCTGCAGTATTCCAGAGATAATCAAAGCTGC
2051  ACAGGTCTCGTCATTTTTATGCAAAGGCGTCCGGAAGGCTCGAACTCTCC
2101  CTTGCACACAAGCCCATCTGTCTGTGCGCCCGGACACGGAAGCA
2151  GGCGGGCGAGCAGCGCCGAGTGGGTCCCCCGTCCCCCGCCACTCACCC
2201  CTCGGCCAACTCTCCGCGCCTTCTCAGCCGCCACCCACGAGGCCGACCTC
2251  TCTCGGCCTAAAAAAAAAAATCCCGGCCTCCCCCTGCACCCCGC
2301  CCGCCGCCCCCAGGGAGCTGCATTAATATTAATCTCGCTGAATAATTGAA
2351  GGCCAGAGATTTATTCGAGCTTCGGCGGAGGGAGCGCAGCTGGGCCG
```

FIG. 1A-2

```
2401  CGTTTAGGCTGCACCACCCGGCGTGTTTCAGCCGCTCGACTCCGCTGGACC
2451  TGGGACCCCCAGAGTGTGGGAGGATGGGGTGGTGTGCCTGTGCCTGTGAGTT
2501  TGGGGGTGAGTGTGAGCTGAAGCGGGTGCTCCGGGAGTGAGGAGGAGC
2551  GCCAGGGGCTGCTCCAGGAGGCGGAGACGGAGGGGCATCCCGGGTCTCC
2601  GCGCGGTCGCGCCTGCGCTTCACCCCGCACGGGGTGACCTGGGCCACGCGG
2651  GCTTCAGGGGAAACAATAGCTACTCCTTAGATCCTGGGCTCCTGCCACCG
2701  GCTGCCCAAGCCCTTCCCGACGAGCGGCGGGAAGGATGGGGGCCTCTTTTCTTATTTGGC
2751  TAATTTATGGCGAGAGGCTGGGGGGCGGTTAAAGGAGTTGCCCGAGGCCGA
2801  CTGAAAAATGGGGGGCGGGGCGGTTAAAGGAGTTGCCCGAGGCGGCG
2851  GCGCGGGTGATGTCAGCTCTCGACGAAAATAGAGAGGATCGCCTGCAAA
2901  TCCCCAGGAGCGCAGCGCTAAACCTTGCAATCCCTCCCCAGGCGCACACCCG
2951  GAGCCAGAGCGCAGCGCTCCACCGTCCTGCCACCACTCTCTGCTCCCGC
3001  CACACGCGCACGCAGCGCTCCACCGTCCTGCCACCACTCTCTGCTCCCGC
3051  CACTCCCGCGCATCGCCGGAGCCCCGTGCGCCCCTTGCAGCCCTGGCAGCGGCTG
3101  CAGGGGCGCATCGCCGGAGCCCCGTGCGCCCCTTGCAGCCCTGGCCATCGCT
3151  CTCTCGGGAAGCCACCTCGGAGCCACCCCGAGCCGCGCCCCGCAAGCGCCA
3201  TCCCCGGCCCCGGAGGGCCAGGAGCCCGTGGAGAGCCGGGAC
3251  GCGGATTAGCGCCCCAGGAGCCTCCTGCGCCCGTTGAGGCGCTAAAGGG
```

FIG. 1A-3

```
3301 CTTACCCCGGAGGGCGGGTGGAAGGGGCGGGCAGAGGCTCCTCTCTTAAATACC
3351 GCTCCCGGCCCGCACTTCGCGCTCACCCCGGCGTCCGCTTTCTCCCTCGCC
3401 CACAGCTGCCGGATAGTGCTGAAGAGAGAGGGGGCGTTCCCCAGACCATGG
3451 CATCTACGGAAGGGTGAGGGGGATTTTATCTGTACCCGCGGGAAAGCGGG
3501 GTCACGCGCGGGGTGGTGCGCGAGGTGGTGCGGGAGCCGTAGCTTGGCTGGGGAT
3551 GCGGCGCGCGGCCCTCGGAGGTGGTGCGGGAGCCGTAGCTTGGCTGGGGAT
3601 GGGATGTGGGGAGGGATTGATTTCTTTCCTGAGATTGCTGCTTAAT
3651 CCTTTGAAAATGCGAGAGGTGGAGGTTGTTTATTTGATAAAAGGGT
3701 AAGGTGCGCTGGGGCCTGAGAGTGTGAGCATAGTGTGAGCAGACAC
3751 CTTTTGGGATTTCAAAACAATAGGGATTGGGCATAGTGTGAGCAGACAC
3801 CGGGTAGCAGCGCCTGGAGCGCGGCGAATGAGCCCAGGCCCGAGGCGGGCTTGC
3851 AGGTGGTGCCGGCTCGGAAGGAATGAGCACAGGCCCAGTTTGCAGGTCGCCAT
3901 GCAAGACCAGCGGCCCCGCTCCGATCGTCTTGTCCCTGGAAGGCGGAATC
3951 GGAGATGCTGGCCCGCTCCGATCGTCTTGTCCCTGGAAGGCGGAATC
4001 TCCCTGGCTAGCTCTAAGGGGTGGACAAGGGTGGACAAGATTTGGGTGCTTCCCGGG
4051 AGGCGGAAAACGTGTGTTTGGACAAGGCAGGAGTCGCCAGACTCCA
4101 GCGGGCAGGATAGCATTGGCTTCCCTATTCAGCCCGAGGATCTGGAGTC
4151 GTGTCCTGCCTCCCAGTTCCAGCTGGCATGGGGAAAGCTCCCTCGCAG
4201 TGATAACTAAAGACAATTGTCTTTAGCACAATGTCTCACACATCAAAGAAAGTCCACAGAG
4251 GGCAAAAGGATTCTTAGATACTCACACATCAAAGAAAGTCCACAGAG
4301 TCCTTGGACCAGTATCTCCCAGAAAACTTTTGGCTTCGTAGAACCTGA
4351 GTGGCAATGAAAGACTGGGCAGCTCAGCGCTTTGGTTAATTCCCAAAAT
4401 TGCAGTTACTCACTTGCAAGCGATCACAAAATCCATGTTATGTGAAAAGC
4451 AAATATCAGGGGCTTCTCTGGGCTCAAGTGGTTGGTGTTTAGGGAATGG
4501 TTTCTCCTAAGAAATTTACCAACTCCGCAGCTGTATCCAAAGCCAGATCTCTAGACTG
4551 ATCTCTAAAACAGGCTGAAGACTGTATCCAAAGCCAGATCTCTAGACTG
4601 CAATCTCCAATAGAAGGAAAATATTTCTAGAACTGTCTCTCTGTCCAGGA
4651 GAAGGAATTCCAGCACACTGGCGCCGTTACTAGTGGATCCGAGCT
```

FIG. 1B

BAC Identification for EAAT2 Mouse

```
   0      57000    114000    171000    226000    285001
C1-24-22902.R                  RPCT-24-22902.F
C1-24-229J15.R                 RPCI-24- 229J15.F
    RPCI-23-293021.R
    RPCI-23-361H22.R                   RPCI-23-361H22.F
    ↗ RPCI-23-161H6.F
       RPCI-24- 203019.F         RPCI-24- 203019.R
         RPCI-23- 350P9.R                  RPCI-23- 360P9.F
         RPCI-23- 114023.R                 RPCI-23- 114023.F
         RPCI-23- 282L23.F
         RPCI-23- 391J1B.R                 RPCI-23- 391J1B.F
         RPCI-24- 369M23.F
         RPCI-24- 369G23.F
           RPCI-23- 350K13.F
              RPCI-24- 315H4.R           RPCI-24- 315H4.F
              RPCI-23- 231K2.F
                 RPCI-24- 398023.F          RPCI-24- 398023.R
              RPCI-23- 270I9.F
           RPCI-24- 186P10.F
           RPCI-24- 318H1.F
             RPCI-23- 469J5.F
             RPCI-23- 34D10.F
                RPCI-23- 408N14.F
                RPCI-24- 307M15.F
                RPCI-24- 222021.R
                  RPCI-24- 127K4.F
                    RPCI-24- 320K8.F
```

BAC clone that will contain full EAAT2 gene and promoter

Input = several hundred kb of genomic sequence

Output = BAC ends that match the input sequence

FIG. 4

SEQUENCE LISTING

<160> NUMBER OF SEQ ID NOS: 4

<210> SEQ ID NO 1
<211> LENGTH: 4696
<212> TYPE: DNA
<213> ORGANISM: Homo sapiens

<400> SEQUENCE: 1

```
aaaaccacca gggttgttgc tggaaagttt ttattcctgg attaaaggca aggatcagcc      60
tgtattttag caatttcttt ttaaggttaa tgtcccatgc gccacctact tctggggccc     120
tgttccagcc cttctttatg tgttgaccac ttctaggtcc agcacttccc aactctgctg     180
cgcagtggac tcaatcccct gggaagtcct taaaaatgc ccaagtcagc cccgcctac      240
ccccaaagat gcatggacca gaaatctctg aaaggtggcc tgagtattac tattttctaa     300
aaggctctct cagaccattt taatgggcac ccagtgttga aaataactgc tccagtttgt     360
taaaaataa ttggtgtgaa tattggcaaa agccctctgg cacaaagaaa gagaaccagt     420
ttcttctagc taatgtttgt tagccagaat tatctgtggc atagtccatg tgacttaata     480
gacctggtct tccagggcag ctgaatgcaa atgtttctca cgtgtagaac gggatgtcag     540
ggcttacaga gaaagtggga aactggaatg atgactccat ctaattcggc catgctggat     600
gattcacctg gattctctca tgtcctgagc attgaaaaca taatgaagag ttttttaaatt    660
gaatgtttaa aagagtgaaa caactccat ccctttttct gtttccttt accttgtatt       720
tatgtaccac caggtacctt gctcttggca gtgagcgtga atgaatggca cagctcagcc    780
cctgaagcct gtgtgcagag attgagggat tgtgatggag tagttcattc atgctcatgt    840
taaggggggt gctaatagca gactagtgct cctgcgatta ttaatatcta ggtctgggac    900
agattgtgat ggcttctttt ccagttgcca cctcagcaga aagggaaata gaaaaccta    960
acttgtaaag ttagacaatt agactgtaaa gtttgtatat gtgacaactt cagatacaaa   1020
gacacacact taccettgac ggggcttaag aggagagtgt caaacataat accaaagtga    1080
aagaagatag ctcttcatct acaaattatt tttaaacaca tttaccaggt taaacaataa    1140
ctaatttttc ggaagagaag agtacccaaa gtcaaatgcc ctaagacgaa gagatgctta    1200
tggcatttt tttaaataa agaaaatgca aagttagagt ggttctgaag gaacctagga     1260
tgaataaggt acagacatga ttattctaat ggtgcagaca ggattgagag agaagggggg    1320
aggggagaga tggagaaagg catggatgga agatgacgtt tggattcaga ttttggaaag    1380
gagagtaaag gaaggaggta agcagagatt tattttttaa attttattaa tgtgttttcc    1440
cctctttttc ttgttatttt tctcatctgt ctgttcatac ttggatattt tgtccaataa    1500
actatcttct aaggactctg aaaatgcact gaatatttt ggagggttta ctggggtgcc    1560
agacgccact ttaggagttt tacatatcct ctccatttca tttagttctc ttagcacaga    1620
gaagtgggag aagatagtcc cattttacag gtgggatgaa gagagagatg gaggaatttg    1680
ccccaggtta ctcagctaga aggtggtgaa gaactcaagc cttcggatat cagcgcctgg    1740
catttaacta ccaatcggtc ctgctgggac tccggctcct ctggcaccat ccccgggacc    1800
tactcagaga gtttgcacgt ggccggtcgc gttccatcgt ctaacaaggt ccagcacagc    1860
gcaaatccga agatcgtcta ccccggggaa aaagagagtc tgtttaattc tcctgtggcc    1920
ctccaagtga gttcttttgg gttccattgc ctagacgagg aaagtgaggc tttgcctgct    1980
ctgcgctcac agggtcggca agtagtggga ccctaggttc ctgcagtatt ccagagataa    2040
tcaaagctgc acaggtctcg tcatttttat gcaaaggcgt ccggaaggct cgaactctcc    2100
cttgcacaag cccatctgtc tctgtgcgcc gccccgggga cacggaagca ggcggcgagc    2160
agcgccgagt gggtggagaa ccgtcccccg ccactcaccc ctcggccaac tctccgcgcc    2220
ttctcagccg gcacccacga ggccgacctc tctcggccta aaaaaaaaa aaaaaaatcc    2280
```

```
cggcctcccc tgcaccccgc ccgccgcccc cagggagctg cattaatatt aatctcgctg   2340
aataattgaa ggccagagat ttattcgagc ttcggcgggg gagggagcgc agctgggccg   2400
cgtttaggct gcaccacccg cgtgtttcag ccgctcgact ccgctggacc tgggaccccc   2460
agacgtggga ggatggggtg ggtgtgcctg cctgtgagtt tgggggtgag tgtgagctga   2520
agcgggtgct ccggggagtg aggagggagc gccaggggct gctccaggga ggcggagacg   2580
gaggggcatc ccgggtctcc cgcgcggtcgc ctgcgcttca ccccgcacgg ggtgacctgg   2640
ggccacgcgg gcttcagggg aaacaatagc tactccttag atcctgggct cctgccaccg   2700
gctgcccaag ccttcccgga cgagcggcgg ggcctctttt cttatttggc taatttatgg   2760
cgagaggctg ggggaaggga tggcagagga gggaccgcga ctgaaaatgg gggcgggggg   2820
cggcggttaa aggagttgcc cgaggcgcg gcgcgggtga tgtcagctct cgacgaaaat   2880
agagagggat cgcctgcaaa tccccagctc cggcggggct aaaccttgca atccctccct   2940
ggccggcgcc gagccagagc gcagcggcct ccaccgcctc cccaggcgcg cacacacccg   3000
cacacgcgca cgcacgctca ccgtcctctg ccaccactct ctgctcccgc cactcgccgc   3060
gcccgcgagc cccgcagcaa agcacaggtg gcagcggctg cagggcgca tcgccggcgt   3120 gcgccctcct gcagccctgg gcgcatcgct ctctcgggga agccaccctc ggagccccg   3180 gagctccccg ccaagcgcca tccccgcggg cggaggggag cgcgggtcgc gcgccgtgga   3240
gagccgggac gcggattagc gcccgcagga gcctcctgcg cccgttgagg cgctaaaggg   3300
cttaccccgg aggcgggtgg aagggcgggc agaggctcct cttaaatacc gctcccggcc   3360
gcacttcgcg ctcaccccgg cgtccgcttt ctccctcgcc cacagctgcc ggatagtgct   3420
gaagaggagg gggcgttccc cagaccatgg catctacgga aggtgaggg gattttatc    3480 tgtacccgcg ggaaagcggg gtcacgcgcg gggtggtggc gccctatcc gggatgcgga   3540 tagagaggcg gcgcggcgg gcctcggagg tggtggcgga gccgtagctt ggctggggat   3600
gggatggtgg ggagggatt gattttcttt cctggagatt gctgcttaat cctttgaaaa   3660
tgcgagaggt ggagggttgt tttattttga taaaaagggt aaggtgcgct ggggccctga   3720
gagtgtgagg aagaaatcct cttgaggtta cttttgggat ttcaaaacaa taggggattg   3780
ggcatagtgt gagcagacac cggggtagca gcgcctggag cgcggcgccc caggcccgag   3840
gcgggcttgc aggtggtgcc ggctcggaag gaatgagcca agacagggcc ctggggcggg   3900
gcaaggacca gcgcgcgcgg ccttgaacgc caggtttgca gagtcgccat ggagatgctg   3960
ggcccgctcc gatcggtcct tgtccctgga aggcggaatc tccctggcta gctctaagga   4020
agggtggaag agatttgggt gcttcccggg aggcgggaaa acgtgtggtt tgggacaagg   4080
gcaggagtcg ccagactcca gcgggcaggg atagcattgg cttccctatt cagcccgagg   4140
atctggagtc gtgtcctgcc tcccaagatt ccagctggca tggggaaagc tccctcgcag   4200
tgataactaa agacaattgt cttagcaag agacagaagg ggctgcaggg ggcaaaagga   4260
ttctttgaat actcacacat caaaggaaag gtccacagag tccttggacc agtatctccc   4320
agaaaacttt tgggcttcg tagaacctga gtggcaatga aaagactggg cagctcagcc   4380
ctttggttaa ttcccaaaat tgcagttact cacttgcaag cgatcacaaa atccatgtta   4440
tgtgaaaagc aaatatcagg ggcttctctg ggctcaagtg gtggtgttgg cattttccag   4500
tttctcctaa gaaatttac caactccgca ggcttgtttt aggggaatgg atctctaaac   4560
aggctgaaga gctggtatcc aaagccagat ctctagactg caatctccaa tagaaggaaa   4620
atatttctag aactgtctct ctgtccagga gaaggaattc cagcacactg gcggccgtta   4680
```

```
ctagtggatc cgagct                                                  4696

<210> SEQ ID NO 2
<211> LENGTH: 2718
<212> TYPE: DNA
<213> ORGANISM: Homo sapiens

<400> SEQUENCE: 2
ggtaccttgc tcttggcagt gagcgtgaat gaatggcaca gctcagcccc tgaagcctgt      60
gtgcagagat tgagggattg tgatggagta gttcattcat gctcatgtta agggggggtgc    120 taatagcaga ctagtgctcc tgcgattatt aatatctagg tctgggacag attgtgatgg    180
cttcttttcc agttgccacc tcagcagaaa gggaaataga aaaccctaac ttgtaaagtt    240
agacaattag actgtaaagt ttgtatatgt gacaacttca gatacaaaga cacacactta    300
cccttgacgg ggcttaagag gagagtgtca aacataatac caaagtgaaa gaagatagct    360
cttcatctac aaattatttt taaacacatt taccaggtta acaataact aattttttcgg    420 aagagaagag tacccaaagt caaatgccct aagacgaaga gatgcttatg cattttttt    480 ttaaataaag aaaatgcaaa gttagagtgg ttctgaagga acctaggatg aataaggtac    540
agacatgatt attctaatgg tgcagacagg attgagagag aagggggggag gggagagatg    600 gagaaaggca tggatggaag atgacgtttg gattcagatt ttggaaagga gagtaaagga    660
aggaggtaag cagagattta ttttttaaat ttattaatg tgttttcccc tcttttttctt    720 gttatttttc tcatctgtct gttcatactt ggatattttg tccaataaac tatcttctaa    780
ggactctgaa aatgcactga atattttttgg agggtttact ggggtgccag acgccacttt    840 aggagttta catatcctct ccatttcatt tagttctctt agcacagaga agtgggagaa    900
gatagtccca ttttacaggt gggatgaaga gagagatgga ggaatttgcc ccaggttact    960
cagctagaag gtggtgaaga actcaagcct tcggatatca cgcgctggca tttaactacc    1020
aatcggtcct gctgggactc cggctcctct ggcaccatcc ccgggaccta ctcagagagt    1080
ttgcacgtgg ccggtcgcgt tccatcgtct aacaaggtcc agcacagcgc aaatccgaag    1140
atcgtctacc ccgggggaaaa agagagtctg tttaattctc ctgtggccct ccaagtgagt    1200
tcttttgggt tccattgcct agacgaggaa agtgaggctt tgcctgctct gcgctcacag    1260
ggtcggcaag tagtgggacc ctaggttcct gcagtattcc agagataatc aaagctgcac    1320
aggtctcgtc atttttatgc aaaggcgtcc ggaaggctcg aactctccct tgcacaagcc    1380
catctgtctc tgtgcgccgc ccccgggaca cggaagcagg cggcgagcag cgccgagtgg    1440
gtggagaacc gtccccgcc actcacccct cggccaactc tccgcgcctt tcagccggc    1500 acccacgagg ccgacctctc tcggcctaaa aaaaaaaaaa aaaaatcccg gcctcccctg    1560
caccccgccc gccgccccca gggagctgca ttaatattaa tctcgctgaa taattgaagg    1620
ccagagattt attcgagctt cggcggggga gggagcgcag ctgggccgcg tttaggctgc    1680
accacccgcg tgtttcagcc gctcgactcc gctggacctg gaccccccag acgtgggagg    1740
atggggtggg tgtgcctgcc tgtgagtttg gggtgagtg tgagctgaag cgggtgctcc    1800
ggggagtgag gagggagcgc caggggctgc tccaggagg cggagacgga ggggcatccc    1860
gggtctccgc gcggtcgcct gcgcttcacc ccgcacgggg tgacctgggg ccacgcgggc    1920
ttcaggggaa acaatagcta ctccttagat cctgggctcc tgccaccggc tgcccaagcc    1980 ttccccggacg agcggcgggg cctctttttct tatttggcta atttatggcg agaggctggg    2040
```

-continued

```
ggaagggatg gcagaggagg gaccgcgact gaaaatgggg gcgggggggcg gcggttaaag    2100
gagttgcccg aggcggcggc gcgggtgatg tcagctctcg acgaaaatag agagggatcg    2160
cctgcaaatc cccagctccg gcggggctaa accttgcaat ccctccctgg ccggcgccga    2220
gccagagcgc agcggcctcc accgcctccc caggcgcgca cacacccgca cacgcgcacg    2280
cacgctcacc gtcctctgcc accactctct gctcccgcca ctcgccgcgc ccgcgagccc    2340
cgcagcaaag cacaggtggc agcggctgca ggggcgcatc gccggcgtgc gccctcctgc    2400
agccctgggc gcatcgctct ctcggggaag ccaccctcgg agcccccgga gctccccgcc    2460
aagcgccatc cccgcgggcg gaggggagcg cgggtcgcgc gccgtggaga gccgggacgc    2520
ggattagcgc ccgcaggagc ctcctgcgcc cgttgaggcg ctaaagggct taccccggag    2580
gcgggtggaa gggcgggcag aggctcctct taaataccgc tcccggccgc acttcgcgct    2640
cacccccggcg tccgctttct ccctcgccca cagctgccgg atagtgctga agaggagggg    2700
gcgttcccca gaccatgg                                                  2718

<210> SEQ ID NO 3
<211> LENGTH: 2454
<212> TYPE: DNA
<213> ORGANISM: Homo sapiens

<400> SEQUENCE: 3
ggtaccttgc tcttggcagt gagcgtgaat gaatggcaca gctcagcccc tgaagcctgt      60
gtgcagagat tgagggattg tgatggagta gttcattcat gctcatgtta agggggggtgc   120
taatagcaga ctagtgctcc tgcgattatt aatatctagg tctgggacag attgtgatgg   180
cttcttttcc agttgccacc tcagcagaaa gggaaataga aaaccctaac ttgtaaagtt   240
agacaattag actgtaaagt ttgtatatgt gacaacttca gatacaaaga cacacactta   300
cccttgacgg ggcttaagag gagagtgtca aacataatac caaagtgaaa gaagatagct   360
cttcatctac aaattatttt taaacacatt taccaggtta acaataact aattttttcgg   420
aagagaagag tacccaaagt caaatgccct aagacgaaga gatgcttatg gcattttttt   480
ttaaataaag aaaatgcaaa gttagagtgg ttctgaagga acctaggatg aataaggtac   540
agacatgatt attctaatgg tgcagacagg attgagagag aagggggggag gggagagatg   600
gagaaaggca tggatggaag atgacgtttg gattcagatt ttggaaagga gagtaaagga   660
aggaggtaag cagagattta ttttttaaat tttattaatg tgttttcccc tcttttttctt   720
gttattttttc tcatctgtct gttcatactt ggatattttg tccaataaac tatcttctaa   780
ggactctgaa aatgcactga atattttttgg agggtttact ggggtgccag acgccacttt   840
aggagtttta catatcctct ccatttcatt tagttctctt agcacagaga agtgggagaa   900
gatagtccca ttttacaggt gggatgaaga gagagatgga ggaatttgcc ccaggttact   960
cagctagaag gtggtgaaga actcaagcct tcggatatca gcgcctggca tttaactacc   1020
aatcggtcct gctgggactc cggctcctct ggcaccatcc ccgggaccta ctcagagagt   1080
ttgcacgtgg ccggtcgcgt tccatcgtct aacaaggtcc agcacagcgc aaatccgaag   1140
atcgtctacc ccggggaaaa agagagtctg tttaattctc ctgtggccct ccaagtgagt   1200
tcttttgggt tccattgcct agacgaggaa agtgaggctt tgcctgctct gcgctcacag   1260
ggtcggcaag tagtgggacc ctaggttcct gcagtattcc agagataatc aaagctgcac   1320
aggtctcgtc attttttatgc aaaggcgtcc ggaaggctcg aactctccct tgcacaagcc   1380
catctgtctc tgtgcgccgc ccccgggaca cggaagcagg cggcgagcag cgccgagtgg   1440
```

```
gtggagaacc gtcccccgcc actcacccct cggccaactc tccgcgcctt ctcagccggc    1500
acccacgagg ccgacctctc tcggcctaaa aaaaaaaaaa aaaatcccg gcctcccctg     1560 caccccgccc gccgccccca gggagctgca ttaatattaa tctcgctgaa taattgaagg    1620
ccagagattt attcgagctt cggcggggga gggagcgcag ctgggccgcg tttaggctgc    1680
accacccgcg tgtttcagcc gctcgactcc gctggacctg gaccccag acgtgggagg      1740 atggggtggg tgtgcctgcc tgtgagtttg ggggtgagtg tgagctgaag cgggtgctcc    1800
ggggagtgag gagggagcgc cagggggctgc tccaggagg cggagacgga ggggcatccc    1860
gggtctccgc gcggtcgcct gcgcttcacc ccgcacgggg tgacctgggg ccacgcgggc    1920
ttcaggggaa acaatagcta ctccttagat cctgggctcc tgccaccggc tgcccaagcc    1980
ttcccggacg agcggcgggg cctctttctt tatttggcta atttatggcg agaggctggg    2040
ggaagggatg gcagaggagg gaccgcgact gaaaatgggg gcggggggcg gcggttaaag    2100
gagttgcccg aggcggcggc gcgggtgatg tcagctctcg acgaaaatag agagggatcg    2160
cctgcaaatc cccagctccg gcgggctaa accttgcaat ccctcctgg ccggcgccga      2220 gccagagcgc agcggcctcc accgcctccc caggcgcgca cacccgca cacgcgcacg      2280 cacgctcacc gtcctctgcc accactctct gctcccgcca ctcgccgcgc ccgcgagccc    2340
cgcagcaaag cacaggtggc agcggctgca ggggcgcatc gccggcgtgc gccctcctgc    2400
agccctgggc gcatcgctct ctcggggaag ccaccctcgg agccccgga gctc           2454

<210> SEQ ID NO 4
<211> LENGTH: 861
<212> TYPE: DNA
<213> ORGANISM: Homo sapiens

<400> SEQUENCE: 4
cccgggtctc cgcgcggtcg cctgcgcttc acccgcacg gggtgacctg gggccacgcg       60
ggcttcaggg gaaacaatag ctactcctta gatcctgggc tcctgccacc ggctgcccaa     120
gccttcccgg acgagcggcg gggcctcttt tcttatttgg ctaatttatg gcgagaggct     180 ggggggaaggg atggcagagg agggaccgcg actgaaaatg ggggcggggg gcggcggtta    240
aaggagttgc ccgaggcggc ggcgcgggtg atgtcagctc tcgacgaaaa tagagaggga    300
tcgcctgcaa atccccagct ccggcggggc taaaccttgc aatccctccc tggccggcgc    360
cgagccagag cgcagcggcc tccaccgcct ccccaggcgc gcacacaccc gcacacgcgc    420
acgcacgctc accgtcctct gccaccactc tctgctcccg ccactcgccg cgccgcgag    480 ccccgcagca aagcacaggt ggcagcggct gcagggcgc atcgccggcg tgcgccctcc    540
tgcagccctg ggcgcatcgc tctctcgggg aagccaccct cggagccccc ggagctcccc    600
gccaagcgcc atcccgcgg gcggaggga gcgggtcg cgcgccgtgg agagccggga        660
cgcggattag cgcccgcagg agcctcctgc gcccgttgag gcgctaaagg gcttaccccg    720
gaggcgggtg gaagggcggg cagaggctcc tcttaaatac cgctcccggc cgcacttcgc    780
gctcaccccg gcgtccgctt tctccctcgc ccacagctgc cggatagtgc tgaagaggag    840
ggggcgttcc ccagaccatg g                                              861
```

EAAT2 PROMOTER AND USES THEREOF

RELATED APPLICATIONS

This instant application is a 371 of PCT/US03/04414, filed Feb. 14, 2003, which claims benefit of U.S. Provisional Application 60/357,179, filed Feb. 15, 2002, the entire contents of which are incorporated herein by this reference.

BACKGROUND OF THE INVENTION

1. Field of the Invention

The present invention features the EAAT2 promoter and uses thereof. In one aspect, the invention relates to novel nucleic acid molecules comprising the EAAT2 promoter. In a related aspect, the invention provides methods for identifying, analyzing, and using the polynucleotides. Further provided are screening methods for detecting therapeutic compounds with capacity to treat neurological disorders.

2. Background

Neurological disorders can significantly impact the central nervous system (CNS) and motor neuron units. For example, certain neurological disorders of the CNS are known to adversely affect the brain and associated structures. Neurological disorders affecting motor neuron units have been grouped into motor neuron diseases and peripheral neuropathies. See generally Kandel, E. R. et al; (1991) in *Principles of Neuroscience*, Appleton & Lange, Norwalk, Conn.; and Rowland, L. P. (ed.) (1982) in *Human Motor Neuron Diseases*, New York, Raven Press.

An illustrative motor neuron disease is amyotrophic lateral sclerosis (ALS). ALS has been reported to be a chronic neuromuscular disorder having recognized clinical manifestations. For example, it has been suggested that degeneration of cortical and spinal/bulbar motor neurons may play a key role in the disorder. ALS is nearly always fatal. About 95% of all ALS cases are sporadic, with many of the remaining cases showing autosomal dominant inheritance. See e.g., Kuncl R. W. et al., (1992) *Motor Neuron Diseases in Diseases of the Nervous System*, Asbury et al. eds. (Philadelphia W. B. Saunders) pp. 1179-1208; Brown, R. H., (1996) *Amer. Neurol.* 30:145; Siddique, T. and Deng., H. X. (1996) Hum. Mol. Genetics 5:1465).

Specific CNS disorders have been also described. In particular, some have been attributed to cholinergic, dopaminergic, adrenergic, serotonergic deficiencies or combinations thereof. CNS disorders of severe impact include pre-senile dementia (sometimes referred to as Alzheimer's disease (AD) or early-onset Alzheimer's disease), senile dementia (dementia of the Alzheimer's type), Parkinson's disease (PD), and Huntington's disease (HD, sometimes referenced as Huntington's chorea). Such CNS disorders are well-represented in the human population. See generally; Gusella, J. F. et al. (1983) *Nature* 306: 234; Borlauer. W. and Jprmuloewoca. P. (eds.) (1976); *Adv. in Parkinsonism: Biochemistry, Physiology, Treatment. Fifth International Symposium on Parkinson's Disease* (Vienna) Basel: Roche; and references cited therein.

Significant attention has been directed towards understanding the etiology of motor neuron diseases. For example, abnormal levels of certain excitotoxic neurotransmitters have been reported to adversely contribute to many motor neuron diseases. In particular, glutamate-mediated excitotoxicity is recognized to have a critical role in ALS. See e.g., Rothstein J. D. et al., (1990) *Ann. Neurol.* 28: 18.; Rothstein J. D. et al. (1992) *N. Engl. Med.* 326: 1464; Rothstein J. D. et al. (1993) *PNAS (USA)* 90: 6591; and Lacomblez, L. et al., (1996) *Lancet* 347: 1179.

There has been substantial efforts towards understanding mechanisms for reducing glutamate levels in the nervous system. For example, high-affinity, sodium-dependent glutamate transport is one reported means of inactivating glutamate. In particular, astrocytic excitatory amino acid transporter 2 (EAAT2) proteins are believed to have substantial functions in that inactivation. See e.g., Rothstein J. D. et al. (1994) *Neuron* 28: 18; Rothstein J. D. et al., (1995) *Ann. Neurol.* 38: 78, and references cited therein.

In particular, investigations have suggested that EAAT2 is a predominant glutamate transporter. More particularly, certain antisense knockdown studies have been reported to demonstrate that EAAT2 loss can lead to excitotoxic neuronal degeneration and progressive motor impairment. Studies of ALS and other neurodegenerative disorders have related impaired glutamate transport to loss of the EAAT2 protein. In particular, up to 60% to 70% of the sporadic ALS patients examined have a 30% to 95% loss of the EAAT2 protein. See e.g., Haugeto et al., supra; Rothstein J. D., et al., (1996) *Neuron* 16: 675; Bristol, L. A. and Rothstein, J. D. (1996) *Ann. Neurol.* 39: 676.

There have been attempts to treat or prevent neurological disorders of the CNS and the motor neuron units. However, most existing therapies do not always stem the development or severity of the disorders in afflicted patients. See e.g., Rowell, (1987) *Adv. Behav. Biol.* 31: 191; Rinne, et al. *Brain Res.* (1991) 54: 167; U.S. Pat. No. 5,210,076 to Berliner; Yurek, D. M. (1990) *Ann. Rev. Neurosci.* 13: 415, and Rowland et al. supra.

Accordingly, there is a need in the field for effective therapies for treating neurological disorders.

SUMMARY OF THE INVENTION

The present invention is based, at least in part, on the discovery of the sequence of the EAAT2 promoter. Accordingly, the present invention provides nucleic acid molecules comprising the EAAT2 promoter, as well as screening assays useful for identifying compounds which modulate the activity of the EAAT2 promoter, and methods of treating neurological disorders comprising administration of EAAT2 promoter modulators.

In one embodiment, the invention provides an isolated nucleic acid molecule which comprises at least a portion of the EAAT2 promoter (e.g., a P1 region, a P2 region, and/or a P3 region), or a complement thereof, wherein the nucleic acid molecule is capable of directing mRNA expression from a promoterless reporter vector. In a preferred embodiment, the EAAT2 promoter comprises at least one SP1 binding site, an E-box motif, a GATA family transcription factor binding site, an NF-κB binding site, a WT1 binding site, a poly(dA:dT) region, a poly(dG:dT) region, and/or a cyclic AMP response element.

In a preferred embodiment, an isolated nucleic acid molecule comprising the EAAT2 promoter includes the nucleotide sequence set forth in SEQ ID NO:1, 2, 3, or 4, or a complement thereof. In another embodiment, an isolated nucleic acid molecule of the invention comprises a nucleotide sequence which is at least about 50%, 55%, 60%, 65%, 70%, 75%, 80%, 85%, 90%, 91%, 92%, 93%, 94%, 95%, 96%, 97%, 98%, 98.5%, 99%, 99.25%, 99.5%, 99.6%, 99.7%, 99.8%, or 99.9% identical to the nucleotide sequence of SEQ ID NO:1, 2, 3, or 4, wherein the nucleic acid molecule is capable of directing mRNA expression from a promoterless reporter vector, or a complement thereof. In still another embodiment, an isolated nucleic acid molecule of the invention comprises at least 30 nucleotides of SEQ ID NO:1, 2, 3, or 4, wherein the nucleic acid molecule is capable of directing mRNA expression from a promoterless reporter vector, or a complement thereof.

In another embodiment, an isolated nucleic acid molecule of the invention comprises an EAAT2 promoter or portion thereof and an operatively linked cDNA molecule, for example, a reporter gene such as EAAT2, luciferase (e.g., firefly luciferase and *Renilla* luciferase), β-galactosidase, chloramphenicol acetyl transferase, or a fluorescent protein (e.g., green fluorescent protein, enhanced green fluorescent protein, red fluorescent protein, yellow fluorescent protein, enhanced yellow fluorescent protein, blue fluorescent protein, or cyan fluorescent protein).

In other embodiments, the invention provides vectors, including expression vectors and host cells comprising the nucleic acid molecules of the invention, as well as methods of producing and/or detecting mRNA and polypeptides (e.g., reporter mRNA and polypeptides) encoded by DNA molecules controlled by the EAAT2 promoter. The invention furher provides methods of detecting the presence of the EAAT2 promoter.

In another embodiment, the invention provides methods of identifying compounds capable of modulating EAAT2 promoter activity to thereby identify compounds capable of treating neurological disorders and psychiatric disorders.

In still other embodiments, the invention provides methods of treating a subject having a neurological or psychiatric disorder comprising administering to the subject a therapeutically effective amount of an EAAT2 promoter modulator, thereby treating said subject having a neurological or psychiatric disorder.

Other features and advantages of the invention will be apparent from the following detailed description and claims.

BRIEF DESCRIPTION OF THE DRAWINGS

FIGS. 1A-1B depicts the nucleotide sequence of the EAAT2 promoter region (SEQ ID NO:1).

FIG. 4 depicts the BAC clone to be used in the generation of EAAT2 promoter BAC transgenic mice.

DETAILED DESCRIPTION OF THE INVENTION

Figure 2:
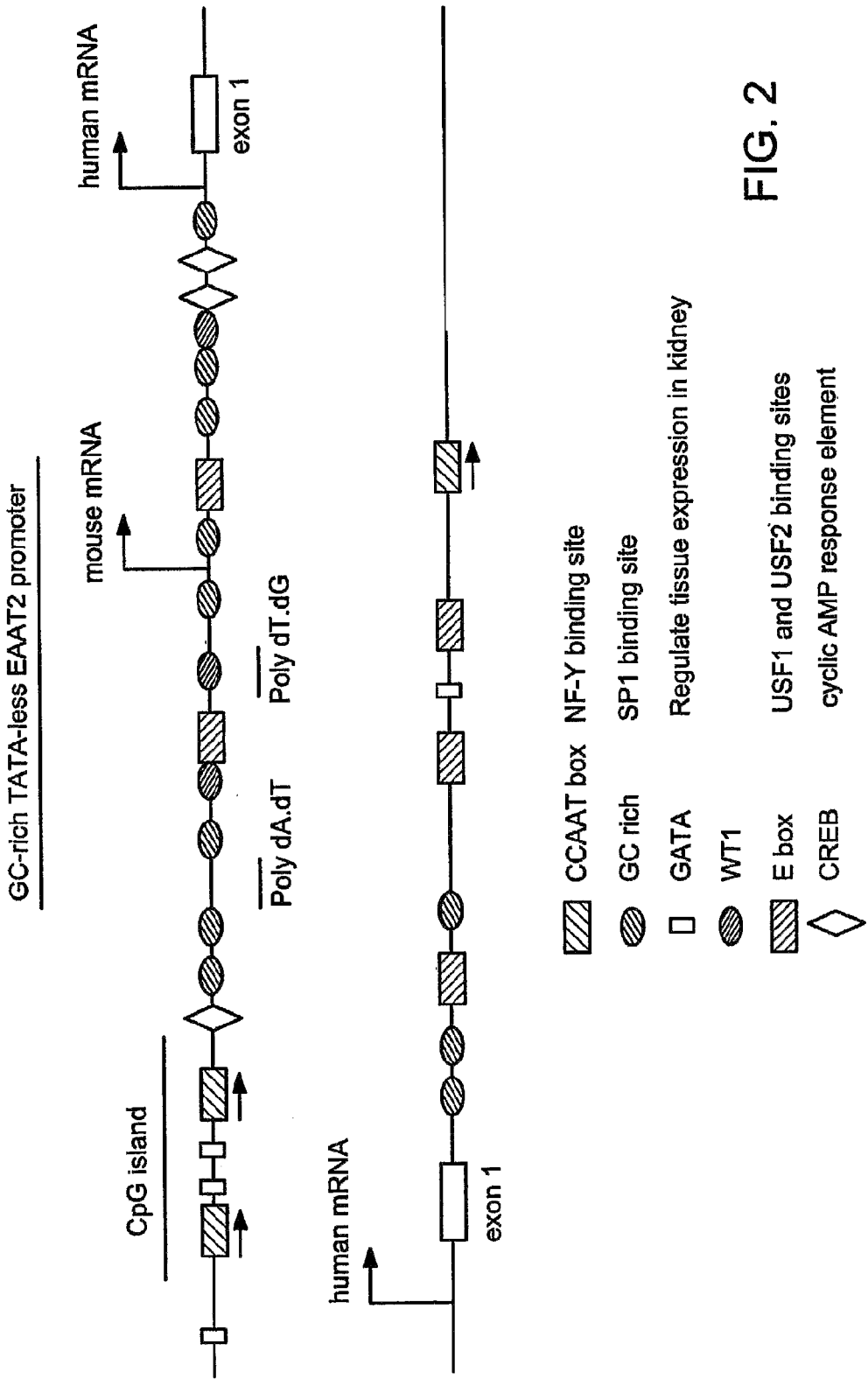
FIG. 2 depicts a schematic representation of the EAAT2 promoter region showing the identified promoter elements.

The present invention is based, at least in part, on the discovery of the sequence of the EAAT2 promoter. Accordingly, the present invention provides nucleic acid molecules comprising the EAAT2 promoter, as well as screening assays useful for identifying compounds which modulate the activity of the EAAT2 promoter, and methods of treating neurological and psychiatric disorders comprising administration of EAAT2 promoter modulators.

The acidic amino acids glutamate (Glu) and aspartate are the predominant excitatory neurotransmitters in the mammalian central nervous system (CNS). Although there are millimolar concentrations of these excitatory amino acids (EAAs) in the brain, extracellular concentrations are maintained in the low micromolar range to facilitate crisp synaptic transmission and to limit the neurotoxic potential of these EAAs. A family of $Na^+$-dependent high affinity transporters is responsible for the regulation and clearance of extracellular EAAs.

Glutamate and aspartate activate ligand-gated ion channels that are named for the agonists N-methyl-D-aspartate (NMDA), a-amino-3-hydroxy-5-methyl-4-isoxazolepropionate (AMPA), and kainate. These ionotropic EAA receptors mediate rapid synaptic depolarization and are important for a number of other physiological processes, including synaptic plasticity and synapse development. The EAAs also activate a family of metabotropic receptors coupled through G-proteins to second messenger systems or ion channels. It is well established that the EAAs are extremely important for normal brain function. However, there is substantial evidence that an extracellular accumulation of EAAs and excessive activation of EAA receptors also contributes to the neuronal cell death observed in acute insults to the CNS. The process known as, 'excitotoxicity', may also contribute to neuronal loss observed in chronic neurodegenerative diseases, including amyotrophic lateral sclerosis (ALS).

The intracellular concentrations of glutamate (5-10 mM) and aspartate (1-5 mM) are 1000-fold to 10,000-fold greater than the extracellular concentrations (<1-10 µM). Unlike many other neurotransmitters, there is no evidence that glutamate or aspartate is metabolized extracellularly. Instead, they are cleared from the extracellular space by transport into neurons and astrocytes.

Several subtypes of $Na^+$-dependent glutamate transporters have been identified through pharmacological strategies and cDNA cloning. Five known distinct cDNA clones that express $Na^+$-dependent high-affinity glutamate transport are referred to herein as GLT-1/EAAT2, EAAC1/EAAT3, GLAST/EAAT1, EAAT4, and EAAT5. There is also evidence for additional heterogeneity of GLT-1 and GLAST that originates from alternate mRNA splicing.

Expression of two of these transporters, GLT-1 and GLAST, is generally restricted to astroglia. Expression of two other transporters, EAAC1 and EAAT4, is generally restricted to neurons, and EAAT5 is thought to be restricted to retina Of the three transporters found in forebrain (GLT-1, GLAST, and EAAC1), GLT-1 appears to be the only transporter that is specific to brain tissue, suggesting that GLT-1 expression is controlled by brain specific mechanisms.

Previously, it was thought that presynaptic transporters had a major role in the clearance of EAAs during synaptic transmission. This was based on the evidence that activity is enriched 2-fold in synaptosomal membrane preparations compared to fractions enriched in mitochondria or myelin. However, it is now known that these membrane preparations contain resealed glial membranes and tremendous amounts of GLT-1 protein. In addition, it has long been known that lesions of specific afferents result in a decrease in $Na^+$-dependent transport in target areas. For example, lesions of the cortical projections to the striatum result in decreased uptake in striatal synaptosomes. These types of studies suggested that there was significant transport into presynaptic terminals, but more recent studies have suggested that these lesions reduce expression of the glial transporters.

Evidence from several complementary strategies strongly suggests that GLT-1 mediates the bulk of $Na^+$-dependent transport of EAAs in the CNS. For example, the pharmacological properties of GLT-1 parallel the predominant component of activity observed in rat brain membranes. Based on the enrichment required to purify GLT-1 to homogeneity, it is thought that GLT-1 represents approximately 1% of total brain protein. Selective immunoprecipitation of GLT-1 from solubilized forebrain tissue and reconstitution of the remaining protein in liposomes, suggests that GLT-1 mediates 90% of transport activity. Anti-sense knock-down of GLT-1 results in the dramatic reductions in synaptosomal transporter activity in several forebrain regions. Synaptosomal uptake in mice genetically deleted of GLT-1 is 5% of normal. Finally, electrophysiological recording of transporter mediated currents in brain preparations strongly suggest that GLT-1 has a primary role for the clearance of glutamate during synaptic transmission in several forebrain regions.

The expression of GLT-1/EAAT2 is dynamically regulated both in vivo and in vitro. Although GLT-1 is the predominant transporter in the adult CNS, expression is rather low early in development and increases during synaptogenesis in both rats and humans. As described above, lesions of projections to a particular target nucleus results in decreased expression of both glial transporters, GLT-1 and GLAST. These data suggest that the presence of neurons induces and/or maintains expression of the glial transporters.

Several different groups have demonstrated decreased expression of GLT-1 and/or GLAST in animal models of acute insults to the CNS, including stroke and traumatic brain injury. A loss in GLT-1 expression has been demonstrated in patients with ALS. Furthermore, there is evidence of decreased expression of these transporters in humans with chronic neurodegenerative diseases, including Alzheimer's Disease, and Huntington's Disease. Loss of GLT-1 is also a feature of the fatal brain tumor, glioblastoma multiforma.

Even though GLT-1 expression is extremely high in vivo, 'normal' astrocytes maintained in culture express essentially no detectable mRNA or protein. Co-culturing astrocytes with neurons induces glial expression of GLT-1, suggesting that neurons induce and/or maintain expression of GLT-1 in vitro. This effect of neurons is, at least in part, mediated by a soluble secreted molecule. Several small molecules mimic this effect of neurons, including dbcAMP, epidermal growth factor, pituitary adenylate cyclase-activating peptide, and immunophilin. In all of these cases the increases in GLT-1 protein expression are accompanied by an increase in GLT-1 mRNA and a change in the morphology of the astrocytes that many believe are reminiscent of differentiation.

The effects of dbcAMP are blocked by an inhibitor of protein kinase A. It has been shown that the increase in GLT-1 expression induced by dbcAMP, epidermal growth factor, or neuron conditioned medium are all blocked by an inhibitor of either phosphatidylinositol 3-kinase or an inhibitor of the transcription factor NF-B. Otherwise, little is known about the mechanisms that actually control GLT-1 expression. Thus, the identification of the EAAT2 promoter provides a valuable tool to understand EAAT2 regulation and to develop assays to control its synthesis.

As used herein, the term "EAAT2" refers to the human astroglial glutamate transporter 2 gene. See, e.g., U.S. Pat. No. 5,658,782 which discloses the human EAAT2 cDNA sequence, the disclosure of the which is specifically incorporated herein by reference. As used herein, the term "GLT-1" refers to the rodent astroglial glutamate transporter 2 gene.

As used herein, the term "promoter" generally refers a region of genomic DNA, usually found 5' to an mRNA transcription start site. Promoters are involved in regulating the timing and level of mRNA transcription and contain, for example, binding sites for cellular proteins such as RNA polymerase and other transcription factors. As used interchangeably herein, the terms "EAAT2 promoter", "EAAT2 promoter region" and the like include the region of genomic DNA found 5' to the EAAT2 mRNA transcription start site. In preferred embodiments, the EAAT2 promoter comprises SEQ ID NO:1, 2, 3, or 4, or fragments thereof. When inserted into a promoterless reporter construct, preferred EAAT2 promoter fragments are able to direct transcription of the reporter gene.

In one embodiment, the EAAT2 promoter includes SEQ ID NO:1 (e.g., nucleotides 1-4696 of SEQ ED NO:1). In another embodiment the EAAT2 promoter includes a P1 region, which comprises nucleotides 733-3450 of SEQ ID NO:1 (also set forth as SEQ ID NO:2). In another embodiment, the EAAT2 promoter includes a P2 region, which comprises nucleotides 733-3186 of SEQ ID NO:1 (also set forth as SEQ ID NO:3). In still another embodiment, the EAAT2 promoter includes a P3 region, which comprises nucleotides 2590-3450 of SEQ ID NO:1 (also set forth as SEQ ID NO:4).

The EAAT2 promoter molecules of the present invention provide novel diagnostic targets and therapeutic agents for neurological and psychiatric disorders. As used herein, the term 'neurological disorder' includes a disorder, disease or condition which affects the nervous system, e.g., the central nervous system. The neurological disorders that can be treated in accord with the present invention include specific disorders that have been reported to be associated with excitotoxicity. Particularly included are specified neurological disorders affecting motor neuron function. Neurological disorders include, but are not limited to, amyotrophic lateral sclerosis (ALS), trinucleotide repeat expansion disorders (e.g., Huntington's disease (HD), spinal and bulbar muscular atrophy, spinocerebellar ataxia types 1, 2, 6, and 7, dentatorubropallidoluysian atrophy, and Machado-Joseph disease), α-synucleinopathies (e.g., Parkinson's disease (PD), dementia with Lewy bodies (DLB), and multiple system atrophy (MSA)), multiple sclerosis (MS), Alzheimer's disease, brain tumors (e.g., glioblastoma), stroke/ischemia, cerebrovascular disease, epilepsy (e.g., temporal lobe epilepsy), HIV-associated dementia, Korsakoff's disease, pain, headaches (e.g., migraine headaches), Pick's disease, progressive supranuclear palsy, Creutzfeldt-Jakob disease, Bell's Palsy, aphasia, sleep disorders, glaucoma, and Meniere's disease.

As used herein, the term 'psychiatric disorder' refers diseases and disorders of the mind, and includes diseases and disorders listed in the Diagnostic and Statistical Manual of Mental Disorders—Fourth Edition (DSM-IV), published by the American Psychiatric Association, Washington D.C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

As noted, neurological and psychiatric disorders of specific interest include those associated with abnormal release or removal of excitotoxic amino acids such as glutamate. Several CNS neuron types are especially adversely affected by excitotoxic glutamate. See e.g., Choi, D. W. (1988) *Neuron* 1: 623; and references cited therein. Specifically preferred neurological disorders include AD, HD, PD with ALS being especially preferred.

I. Isolated Nucleic Acid Molecules

One aspect of the invention pertains to isolated nucleic acid molecules that comprise the EAAT2 promoter or biologically active portions thereof, as well as nucleic acid fragments sufficient for use as hybridization probes to identify EAAT2 promoter containing nucleic acid molecules and fragments for use as PCR primers for the amplification or mutation of EAAT2 promoter nucleic acid molecules. As used herein, the term 'nucleic acid molecule' is intended generally to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

In general, optimal practice of the present invention can be achieved by use of recognized manipulations. For example, techniques for isolating mRNA, methods for making and screening cDNA libraries, purifying and analyzing nucleic acids, methods for making recombinant vector DNA, cleaving DNA with restriction enzymes, ligating DNA, introducing DNA into host cells by stable or transient means, culturing the host cells, methods for isolating and purifying polypeptides and making antibodies are generally known in the field. See generally Sambrook et al., *Molecular Cloning* (2d ed. 1989), and Ausubel et al., *Current Protocols in Molecular Biology*, (1989) John Wiley & Sons, New York.

The term 'isolated nucleic acid molecule' includes nucleic acid molecules which are separated from other nucleic acid molecules which are present in the natural source of the nucleic acid. For example, with regards to genomic DNA, the term 'isolated' includes nucleic acid molecules which are separated from the chromosome with which the genomic DNA is naturally associated. Preferably, an 'isolated' nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated EAAT2 promoter nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an 'isolated' nucleic acid molecule can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, 2, 3, or 4, or a portion thereof, can be isolated using standard molecular biology techniques and the sequence information provided herein. Using all or a portion of the nucleic acid sequence of SEQ ID NO:1, 2, 3 or 4 as hybridization probes, EAAT2 promoter nucleic acid molecules can be isolated using standard hybridization and cloning techniques (e.g., as described in Sambrook, J. et al., supra).

Moreover, a nucleic acid molecule encompassing all or a portion of SEQ ID NO:1, 2, 3, or 4 can be isolated by the polymerase chain reaction (PCR) using synthetic oligonucleotide primers designed based upon the sequence of SEQ ID NO:1, 2, 3, or 4.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to EAAT2 promoter nucleotide sequences can be prepared by standard synthetic techniques, e.g., using an automated DNA synthesizer.

In one embodiment, an isolated nucleic acid molecule of the invention comprises the nucleotide sequence shown in SEQ ID NO:1 (FIGS. 1A-1B). This DNA molecule comprises sequences encoding the human EAAT2 promoter. An isolated nucleic acid molecule of the invention may also comprise nucleotides 733-3450 of SEQ ID NO:1 (also set forth as SEQ ID NO:2). This DNA sequence comprises the P1 region of the EAAT2 promoter. In another embodiment, an isolated nucleic acid molecule of the invention comprises nucleotides 733-3186 of SEQ ID NO:1 (also set forth as SEQ ID NO:3). This DNA molecule comprises the P2 region of the EAAT2 promoter. In still another embodiment, an isolated nucleic acid molecule of the invention comprises nucleotides 2590-3450 of SEQ ID NO:1 (also set forth as SEQ ID NO:4). This DNA molecule comprises the P3 region of the EAAT2 promoter.

In still another embodiment, an isolated nucleic acid molecule of the invention comprises a nucleic acid molecule which is a complement of the nucleotide sequence shown in SEQ ID NO:1, 2, 3, or 4, or a portion of any of these nucleotide sequences. A nucleic acid molecule which is complementary to the nucleotide sequence shown in SEQ ID NO:1, 2, 3, or 4 is one which is sufficiently complementary to the nucleotide sequence shown in SEQ ID NO:1, 2, 3, or 4 such that it can hybridize to the nucleotide sequence shown in SEQ ID NO:1, 2, 3, or 4, thereby forming a stable duplex. The term 'complementary' or like term refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 95% of the nucleotides of the other strand, usually at least about 98%, and more preferably from about 99 to about 100%. Complementary polynucleotide sequences can be identified by a variety of approaches including use of well-known computer algorithms and software.

In still another embodiment, an isolated nucleic acid molecule of the present invention comprises a nucleotide sequence which is at least about 50%, 55%, 60%, 65%, 70%, 75%, 80%, 85%, 90%, 91%, 92%, 93%, 94%, 95%, 96%, 97%, 98% 99%, 99.1%, 99.2%, 99.3%, 99.4%, 99.5%, 99.6%, 99.7%, 99.8%, 99.9% or more identical to the nucleotide sequence shown in SEQ ID NO:1, 2, 3, or 4 (e.g., to the entire length of the nucleotide sequence), or a portion or complement of any of these nucleotide sequences. In one embodiment, a nucleic acid molecule of the present invention comprises a nucleotide sequence which comprises part or all of SEQ ID NO:1, 2, 3, or 4, or a complement thereof, and which is at least (or no greater than) 25, 30, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1250, 1300, 1350, 1400, 1450, 1500, 1550, 1600, 1650, 1700, 1750, 1800, 1850, 1900, 1950, 1994, 2000, 2050, 2073, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3441, 3450, 3500, 3550, 3600, 3650, 3700, 3750, 3800, 3841, 3850, 3900, 3950, 4000, 4050, 4100, 4150, 4200, 4250, 4300, 4350, 4400, 4450, 4500, 4550, 4600, 4650 or more nucleotides (e.g., contiguous nucleotides) in length.

To determine the percent identity of two nucleic acid or amino acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to a nucleotide sequence having 100 nucleotides, at least 30, preferably at least 40, more preferably at least 50, even more preferably at least 60, and even more preferably at least 70, 80, or 90 nucleotides are aligned). The amino acid residues or nucleotides at corresponding amnino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package (available at online through the Genetics Computer Group), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at online through the Genetics Computer Group), using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of Meyers and Miller (Comput. Appl. Biosci. 4:11-17 (1988)) which has been incorporated into the ALIGN program (version 2.0 or version 2.0U), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul et al. (1990) J. Mol. Biol. 215:403-10. BLAST nucleotide searches can be performed with the NBLAST program, score=100, wordlength=12 to obtain nucleotide sequences homologous to EAAT2 nucleic acid molecules of the invention. BLAST protein searches can be performed with the XBLAST program, score=50, wordlength=3 to obtain amino acid sequences homologous to EAAT2 protein molecules of the invention. To obtain gapped alignments for comparison purposes, Gapped BLAST can be utilized as described in Altschul et al. (1997) Nucleic Acids Res. 25(17):3389-3402. When utilizing BLAST and Gapped BLAST programs, the default parameters of the respective programs (e.g., XBLAST and NBLAST) can be used. See the website for the National Center for Biotechnology Information.

The nucleic acid molecule of the invention can comprise only a portion of the nucleic acid sequence of SEQ ID NO:1, 2, 3, or 4, for example, a fragment which can be used as a probe or primer or a fragment encoding a portion of an EAAT2 promoter. The probe/primer (e.g., oligonucleotide) typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, 2, 3, or 4, or a complement thereof.

Exemplary probes or primers are at least (or no greater than) 12 or 15, 20 or 25, 30, 35, 40, 45, 50, 55, 60, 65, 70, 75 or more nucleotides in length and/or comprise consecutive nucleotides of an isolated nucleic acid molecule described herein. Also included within the scope of the present invention are probes or primers comprising contiguous or consecutive nucleotides of an isolated nucleic acid molecule described herein, but for the difference of 1, 2, 3, 4, 5, 6, 7, 8, 9 or 10 bases within the probe or primer sequence. Probes based on the EAAT2 promoter nucleotide sequences can be used to detect (e.g., specifically detect) genomic sequences. In preferred embodiments, the probe further comprises a label group attached thereto, e.g., the label group can be a radioisotope, a fluorescent compound, an enzyme, or an enzyme co-factor. In another embodiment a set of primers is provided, e.g., primers suitable for use in a PCR, which can be used to amplify a selected region of an EAAT2 promoter sequence, e.g., a domain, region, site or other sequence described herein. The primers should be at least 5, 10, or 50 base pairs in length and less than 100, or less than 200, base pairs in length. The primers should be identical, or differ by no greater than 1, 2, 3, 4, 5, 6, 7, 8, 9 or 10 bases when compared to a sequence disclosed herein or to the sequence of a naturally occurring variant. Such probes can be used as a part of a diagnostic test kit for identifying cells or tissue which misexpress an EAAT2 protein, such as by measuring a level of an EAAT2 promoter activity in a sample of cells from a subject, e.g., determining whether a genomic EAAT2 promoter has been mutated or deleted.

A nucleic acid fragment encoding a portion of an EAAT2 promoter can be prepared by isolating a portion of the nucleotide sequence of SEQ ID NO:1, 2, 3, or 4, inserting the portion of the EAAT2 promoter (e.g., by standard recombinant methods) into a promoterless reporter vector (e.g., a promoterless luciferase reporter vector such as pGL3, available from Promega, Madison, Wis., and assessing the activity of the portion of the EAAT2 promoter to induce luciferase expression (e.g., when transiently transfected into a cell). In an exemplary embodiment, the nucleic acid molecule is at least 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1250, 1300, 1350, 1400, 1450, 1500, 1550, 1600, 1650, 1700, 1750, 1800, 1850, 1900, 1950, 1994, 2000, 2050, 2073, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3441, 3450, 3500, 3550, 3600, 3650, 3700, 3750, 3800, 3841, 3850, 3900, 3950, 4000, 4050, 4100, 4150, 4200, 4250, 4300, 4350, 4400, 4450, 4500, 4550, 4600, 4650 or more nucleotides in length.

In another embodiment, nucleic acid molecules of the invention can comprise variants of the sequences disclosed herein. Nucleic acid variants can be naturally occurring, such as allelic variants (same locus), homologues (different locus), and orthologues (different organism, e.g., mouse) or can be non-naturally occurring. Non-naturally occurring variants can be made by mutagenesis techniques, including those applied to polynucleotides, cells, or organisms. The variants can contain nucleotide substitutions, deletions, inversions and insertions.

Allelic variants result, for example, from DNA sequence polymorphisms within a population (e.g., the human population). Such genetic polymorphism in the EAAT2 promoter may exist among individuals within a population due to natural allelic variation.

Allelic variants of EAAT2 promoter include both functional and non-functional EAAT2 promoters. Functional allelic variants are naturally occurring nucleotide sequence variants of the EAAT2 promoter that maintain the ability to, e.g., drive transcription of the EAAT2 mRNA. Non-functional allelic variants are naturally occurring nucleotide sequence variants of the EAAT2 promoter that do not have the ability to, e.g., drive transcription of the EAAT2 mRNA, ATP, or that induce EAAT2 transcription at levels higher than normally observed.

Nucleic acid molecules corresponding to natural allelic variants and homologues of the EAAT2 promoters of the invention can be isolated based on their homology to the EAAT2 promoter nucleic acids disclosed herein using the nucleic acid sequences disclosed herein, or a portions thereof, as hybridization probes according to standard hybridization techniques under stringent hybridization conditions. Nucleic acid molecules corresponding to natural allelic variants and homologues of the EAAT2 promoters of the invention can further be isolated by mapping to the same chromosome or locus as the EAAT2 gene.

Orthologues, homologues, and allelic variants can be identified using methods known in the art (e.g., by hybridization to an isolated nucleic acid molecule of the present invention, for example, under stringent hybridization conditions). In one embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, 2, 3, or 4. In other embodiments, the nucleic acid is at least 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1250, 1300, 1350, 1400, 1450, 1500, 1550, 1600, 1650, 1700, 1750, 1800, 1850, 1900, 1950, 1994, 2000, 2050, 2073, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3441, 3450, 3500, 3550, 3600, 3650, 3700, 3750, 3800, 3841, 3850, 3900, 3950, 4000, 4050, 4100, 4150, 4200, 4250, 4300, 4350, 4400, 4450, 4500, 4550, 4600, 4650, or more nucleotides in length.

As used herein, the term 'hybridizes under stringent conditions' is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in Current Protocols in Molecular Biology, Ausubel et al., eds., John Wiley & Sons, Inc. (1995), sections 2, 4, and 6. Additional stringent conditions can be found in Molecular Cloning: A Laboratory Manual, Sambrook et al., Cold Spring Harbor Press, Cold Spring Harbor, N.Y. (1989), chapters 7, 9, and 11. A preferred, non-limiting example of stringent hybridization conditions includes hybridization in 4× sodium chloride/sodium citrate (SSC), at about 65-70° C. (or alternatively hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or alternatively hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature (T$_m$) of the hybrid, where T$_m$ is determined according to the following equations. For hybrids less than 18 base pairs in length, T$_m$(° C.)=2(# of A+T bases)+4(# of G+C bases). For hybrids between 18 and 49 base pairs in length, T$_m$(° C.)=81.5+16.6(log$_{10}$[Na$^+$])+0.41(% G+C)−(600/N), where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M NaH$_2$PO$_4$, 7% SDS at about 65° C., followed by one or more washes at 0.02M NaH$_2$PO$_4$, 1% SDS at 65° C. (see e.g., Church and Gilbert (1984) Proc. Natl. Acad. Sci. USA 81:1991-1995), or alternatively 0.2×SSC, 1% SDS.

Preferably, an isolated nucleic acid molecule of the invention that hybridizes under stringent conditions to the sequence of SEQ ID NO:1, 2, 3, or 4 corresponds to a naturally-occurring nucleic acid molecule. As used herein, a 'naturally-occurring' nucleic acid molecule refers to an RNA or DNA molecule having a nucleotide sequence that occurs in nature.

In addition to naturally-occurring allelic variants of the EAAT2 promoter sequences that may exist in the population, the skilled artisan will further appreciate that changes can be introduced by mutation into the nucleotide sequences of SEQ ID NO:1, 2, 3, or 4, without altering the functional ability of the EAAT2 promoter sequences. In one embodiment, the isolated nucleic acid molecule comprises a nucleotide sequence which is at least about 50%, 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to SEQ ID NO:1, 2, 3, or 4, e.g., to the entire length of SEQ ID NO:1, 2, 3, or 4.

II. Recombinant Expression Vectors and Host Cells

Another aspect of the invention pertains to vectors, for example recombinant expression vectors, containing an EAAT2 promoter nucleic acid molecule. As used herein, the term 'vector' refers to a nucleic acid molecule capable of transporting another nucleic acid to which it has been linked. One type of vector is a 'plasmid', which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as 'expression vectors'. In general, expression vectors of utility in recombinant DNA techniques are often in the form of plasmids. In the present specification, 'plasmid' and 'vector' can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, 'operably linked' is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term 'regulatory sequence' is intended to include promoters, enhancers and other expression control elements (e.g. polyadenylation signals). Such regulatory sequences are described, for example, in Goeddel (1990) Methods Enzymol. 185:3-7. Regulatory sequences include those which direct constitutive expression of a nucleotide sequence in many types of host cells and those which direct expression of the nucleotide sequence only in certain host cells (e.g., tissue-specific regulatory sequences). In a preferred embodiment, the regulatory sequences in the expression vectors of the invention are derived from the EAAT2 promoter of the invention, and the nucleic acid sequence to be expressed is a reporter gene, as described elsewhere herein. It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

In a preferred embodiment, a recombinant vector of the invention is a promoterless reporter vector. As used herein, a "promoterless reporter vector" refers to a vector, preferably a plasmid, that contains a reporter gene, but no promoter region capable of driving expression of the reporter gene mRNA. Instead of a promoter, the promoterless reporter vector contains at least one site that can be cleaved by a restriction enzyme, and into which can be inserted a DNA fragment of interest (using standard recombinant DNA methods). The vector can then be tested (e.g., in an in vitro assay or a transient transfection assay) for the ability of the inserted DNA fragment to act as a promoter to drive expression of the reporter gene. Examples of promoterless reporter vectors include, but are not limited to, the pGL3 (Promega, Madison, Wis.), pBBR RESO (MiBiTec, Gottingen, Germany), pAM990, pAM1414, pRL-null Vector (Promega), phRG-B, pDsRed-Express-1 (BD Biosciences/Clontech, Palo Alto, Calif.), pDsRed2-1 (BD Biosciences/Clontech), pECFP-1 (BD Biosciences/Clontech), pEGFP-1 (BD Biosciences/Clontech), pEYFP-1 (BD Biosciences/Clontech), pSVOAT-CAT (see Lok S. et al. (1989) *Nucleic Acids Res.* 17:3563-82), pBLCAT5, pXP2, and pPD96.04. Many of these vectors are available commercially.

As used herein a "reporter" or a "reporter gene" refers to a nucleic acid molecule encoding a detectable marker. Preferred reporter genes include luciferase (e.g., firefly luciferase or *Renilla* luciferase), β-galactosidase, chloramphenicol acetyl transferase (CAT), and a fluorescent protein (e.g., green fluorescent protein, red fluorescent protein, yellow fluorescent protein, blue fluorescent protein, cyan fluorescent protein, or variants thereof, including enhanced variants). In another preferred embodiment, a preferred reporter gene is the EAAT2 gene. Reporter genes must be detectable by a reporter assay. Reporter assays can measure the level of reporter gene expression or activity by any number of means, including measuring the level of reporter mRNA, the level of reporter protein, or the amount of reporter protein activity.

Methods for measuring mRNA levels are well-known in the art and include, but are not limited to, Northern blotting, RT-PCR, primer extension, and nuclease protection assays. Methods for measuring reporter protein levels are also well-known in the art and include, but are not limited to, Western blotting, ELISA, and RIA assays. Reporter activity assays are still further well-known in the art, and include luciferase assays, β-galactosidase, and chloramphenicol acetyl transferase (CAT) assays. Fluorescent protein activity can be measured by detecting fluorescence. EAAT2 (i.e., GLT-1) activity can be measured using a standard glutamate transport assays (described elsewhere herein).

Accordingly, in one embodiment, the invention provides a method for producing mRNA and/or protein molecules (e.g., reporter gene mRNA and/or protein molecules), by culturing in a suitable medium a host cell of the invention (e.g., a mammalian host cell such as a non-human mammalian cell)

containing a recombinant expression vector containing the EAAT2 promoter or a fragment thereof, such that the mRNA and/or protein is produced.

The recombinant expression vectors of the invention are preferably designed for expression in eukaryotic cells (e.g., mammalian cells). Alternatively, the recombinant expression vector can be transcribed and translated in vitro.

Another aspect of the invention pertains to host cells into which an EAAT2 promoter nucleic acid molecule of the invention is introduced, e.g., an EAAT2 promoter nucleic acid molecule within a vector (e.g., a recombinant expression vector) or an EAAT2 promoter nucleic acid molecule containing sequences which allow it to homologously recombine into a specific site of the host cell's genome. The terms 'host cell' and 'recombinant host cell' are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a vector containing an EAAT2 promoter can be propagated and/or expressed in bacterial cells such as *E. coli*, insect cells, yeast or mammalian cells (such as Chinese hamster ovary cells (CHO), COS cells (e.g., COS7 cells), C6 glioma cells, HEK 293T cells, or neurons). Other suitable host cells are known to those skilled in the art.

Vector DNA can be introduced into prokaryotic or eukaryotic cells via conventional transformation or transfection techniques. As used herein, the terms 'transformation' and 'transfection' are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify an d select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an EAAT2 promoter or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an mRNA or protein (e.g., an EAAT2 mRNA or protein, or a reporter mRNA or protein) encoded by the nucleic acid molecule operatively linked to the EAAT2 promoter. Accordingly, the invention further provides methods for producing an mRNA or protein using the host cells of the invention. In one embodiment, the method comprises culturing the host cell of the invention (into which a recombinant expression vector containing the EAAT2 promoter and an operatively linked nucleic acid molecule (e.g., a cDNA molecule) has been introduced) in a suitable medium such that mRNA and/or protein encoded by the operatively linked nucleic acid molecule is produced. In another embodiment, the method further comprises isolating the mRNA and/or protein from the medium or the host cell.

The host cells of the invention can also be used to produce non-human transgenic animals. For example, in one embodiment, a host cell of the invention is a fertilized oocyte or an embryonic stem cell into which EAAT2 promoter sequences have been introduced. Such host cells can then be used to create non-human transgenic animals in which exogenous EAAT2 promoter sequences have been introduced into their genome or homologous recombinant animals in which endogenous EAAT2 promoter sequences have been altered. Such animals are useful for studying the function and/or activity of an EAAT2 promoter and for identifying and/or evaluating modulators of EAAT2 promoter activity. As used herein, a 'transgenic animal' is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a 'homologous recombinant animal' is a non-human animal, preferably a mammal, more preferably a mouse, in which an endogenous EAAT2 promoter has been altered by homologous recombination between the endogenous gene and an exogenous DNA molecule introduced into a cell of the animal, e.g., an embryonic cell of the animal, prior to development of the animal.

A transgenic animal of the invention can be created by introducing an EAAT2 promoter-encoding nucleic acid into the male pronuclei of a fertilized oocyte, e.g., by microinjection or retroviral infection, and allowing the oocyte to develop in a pseudopregnant female foster animal. The EAAT2 promoter cDNA sequence of SEQ ID NO:1, 2, 3, or 4, can be introduced as a transgene into the genome of a non-human animal. Alternatively, a non-human homologue of a human EAAT2 promoter, such as a rat or mouse EAAT2 promoter, can be used as a transgene. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo (Cold Spring Harbor Laboratory Press, Cold Spring Harbor, N.Y., 1986). Similar methods are used for production of other transgenic animals. A transgenic founder animal can be identified based upon the presence of an EAAT2 promoter transgene in its genome and/or expression of a reporter gene operatively linked to the EAAT2 promoter transgene in tissues or cells of the animals. A transgenic founder animal can then be used to breed additional animals carrying the transgene. Moreover, transgenic animals carrying a transgene containing an EAAT2 promoter can further be bred to other transgenic animals carrying other transgenes.

To create a homologous recombinant animal, a vector is prepared which contains at least a portion of an EAAT2 promoter into which a deletion, addition or substitution has been introduced to thereby alter, e.g., functionally disrupt, the EAAT2 promoter. The EAAT2 promoter can be a human gene (e.g., the cDNA of SEQ ID NO:1, 2, 3, or 4), but more preferably, is a non-human homologue of a human EAAT2 promoter. For example, a mouse EAAT2 promoter gene can be used to construct a homologous recombination nucleic acid molecule, e.g., a vector, suitable for altering an endogenous EAAT2 promoter gene in the mouse genome. In a preferred embodiment, the homologous recombination nucleic acid molecule is designed such that, upon homologous recombination, the endogenous EAAT2 promoter is functionally disrupted (i.e., no longer encodes a functional protein; also referred to as a 'knock out' vector). Alternatively, the homologous recombination nucleic acid molecule can be designed such that, upon homologous recombination, the endogenous EAAT2 promoter is mutated or otherwise altered. In the homologous recombination nucleic acid molecule, the altered portion of the EAAT2 promoter is flanked at its 5' and 3' ends by additional nucleic acid sequence from the region of the EAAT2 promoter to allow for homologous recombination to occur between the exogenous EAAT2 promoter carried by the homologous recombination nucleic acid molecule and an endogenous EAAT2 promoter in a cell, e.g., an embryonic stem cell. The additional flanking EAAT2 promoter nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) Cell 51:503 for a description of homologous recombination vectors). The homologous recombination nucleic acid molecule is introduced into a cell, e.g., an embryonic stem cell line (e.g., by electroporation) and cells in which the introduced EAAT2 promoter has homologously recombined with the endogenous EAAT2 promoter are selected (see e.g., Li, E. et al. (1992) Cell 69:915). The selected cells can then be injected into a blastocyst of an animal (e.g., a mouse) to form aggregation chimeras (see e.g., Bradley, A., in Teratocarcinomas and Embryonic Stem Cells: A Practical Approach, Robertson, E. J. ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) Curr. Opin. Biotechnol. 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

Clones of the non-human transgenic animals described herein can also be produced according to the methods described in Wilmut, I. et al. (1997) Nature 385:810-813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

Transgenic and homologous recombinant animals of the invention can also be used to produce stable cell lines containing the EAAT2 promoter. Such cell lines are useful because they can be made so that they do not overexpress the transgene (as may happen in transient transfection), and therefore more closely reflect the natural cellular environment of the transgene. Such cell lines may be produced by isolating cells (e.g., fibroblasts or astroglial cells) from a transgenic or homologous recombinant animal (e.g., a mouse) and culturing them using standard methods. In some embodiments primary (i.e., non-immortalized) cells are preferred, or the cells may be may be immortalized (e.g., by the addition of a gene such as SV40 large T antigen) in order to propagate them indefinitely in culture.

As used interchangeably herein the terms 'standard glutamate assay' or 'standard glutamate transport assay' (or like terms) are meant to include one or more of the following steps:

a) introducing a recombinant expression vector comprising the EAAT2 cDNA into a suitable host cells such as COS-7 cells, b) adding detectably-labeled glutamate; and c) detecting glutamate transport in the cells.

Typically, the standard glutamate assay is a sodium-dependent glutamate transport assay. Introduction of the recombinant vectors in accord with the standard glutamate assay can be conducted by any acceptable means, e.g., retroviral transfer, viral or bacteriophage infection, calcium-, liposome-, DEAE or polybrene-mediated transfection, biolistic transfer, or other techniques known in the art. See Sambrook, et al. supra; Ausubel, et al. supra.

In one embodiment of the standard glutamate assay, the test and control cells are washed following introduction of the recombinant vector and then incubated with a suitable amount of detectably-labeled glutamate, e.g., $^3$H-labeled glutamate (DuPont-NEN) and non-labeled glutamate. Following a suitable incubation interval, test and control cells are washed several times in a suitable wash buffer such as ice-cold PBS, solublized in a solution comprising about 0.1% SDS and the amount of radioactivity associated with the cells determined using conventional scintillation counting methods.

An especially preferred glutamate transport assay has been disclosed by Rothstein et al. (1995) Ann. Neurol. 38: 78. See also Rothstein et al. (1992) N. Engl. J. Med. 326: 1464. The disclosures of which are specifically incorporated by reference.

III. Screening Assays

The invention provides a method (also referred to herein as a "screening assay") for identifying modulators, i.e., candidate or test compounds or agents (e.g., nucleic acids, peptides, peptidomimetics, small molecules, or other drugs) which bind to the EAAT2 promoter, and/or which have a stimulatory or inhibitory effect on, for example, EAAT2 promoter activity.

In one embodiment, the invention provides assays for screening candidate or test compounds which are modulators EAAT2 promoter activity. In another embodiment, the invention provides assays for screening candidate or test compounds which bind to or modulate the activity of an EAAT2 promoter. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:45).

Examples of methods for the synthesis of molecular libraries can be found in the art, for example, in: DeWitt et al. (1993) Proc. Natl. Acad. USA 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten ( 992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc. Natl. Acad. Sci. USA 89:1865-1869) or on phage (Scott and Smith (1990) Science 249:386-390); (Devlin (1990) Science 249:404-406); (Cwirla et al. (1990) Proc. Natl. Acad. Sci. USA 87:6378-6382); (Felici (1991) J. Mol. Biol. 222:301-310); (Ladner supra.).

In a preferred embodiment, an assay is a cell-based assay in which a cell which expresses a reporter gene operatively linked to an EAAT2 promoter or portion thereof (e.g., whose expression is under the control of the EAAT2 promoter or portion thereof) is contacted with a test compound and the ability of the test compound to modulate EAAT-2 promoter activity is determined. Determining the ability of the test compound to modulate EAAT2 promoter activity can be accomplished by monitoring reporter gene expression (e.g., reporter mRNA or polypeptide expression level) or activity, for example. As described elsewhere herein, the reporter can be any detectable marker. For example, the reporter can be a nucleic acid sequence, the expression of which can be measured by, for example, Northern blotting, RT-PCR, primer extension, or nuclease protection assays. The reporter may also be a nucleic acid sequence that encodes a polypeptide, the expression of which can be measured by, for example, Western blotting, ELISA, or RIA assays. Reporter expression can also be monitored by measuring the activity of the polypeptide encoded by the reporter using, for example, a standard glutamate transport assay, a luciferase assay, a β-galactosidase assay, a chloramphenicol acetyl transferase (CAT) assay, or a fluorescent protein assay.

The level of expression or activity of a reporter under the control of the EAAT2 promoter in the presence of the candidate compound is compared to the level of expression or activity of the reporter in the absence of the candidate compound. The candidate compound can then be identified as a modulator of EAAT2 promoter activity based on this comparison. For example, when expression of reporter mRNA or protein expression or activity is greater (statistically significantly greater) in the presence of the candidate compound than in its absenice, the candidate compound is identified as a stimulator of EAAT2 promoter activity. Alternatively, when expression or activity of reporter mRNA or protein is less (statistically significantly less) in the presence of the candidate compound than in its absence, the candidate compound is identified as an inhibitor of EAAT2 promoter activity.

The ability of the test compound to bind to the EAAT2 promoter and/or to modulate the binding of proteins (e.g., transcription factors) to the EAAT2 promoter can also be determined. Determining the ability of the test compound to bind to and/or modulate EAAT2 promoter binding to a binding protein can be accomplished, for example, by coupling the test compound, the EAAT2 promoter or the binding protein with a radioisotope or enzymatic label such that binding of the EAAT2 promoter to the test compound or the binding protein can be determined by detecting the labeled component in a complex. For example, compounds (e.g., the test compound, the EAAT2 promoter, or a binding protein) can be labeled with $^{32}$p, 125I, $^{35}$S, $^{14}$C, or $^{3}$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a test compound or EAAT2 promoter binding protein) to interact with the EAAT2 promoter without the labeling of any of the interactants. For example, a microphysiometer can be used to detect the interaction of a compound with the EAAT2 promoter without the labeling of either the compound or the EAAT2 promoter (McConnell, H. M. et al. (1992) Science 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and the EAAT2 promoter.

In another embodiment, the assay is a cell-free assay in which an EAAT2 promoter or portion thereof is contacted with a test compound and the ability of the test compound to modulate (e.g., stimulate or inhibit) the activity of the EAAT2 promoter or portion thereof is determined. Determining the ability of the test compound to modulate the activity of an EAAT2 promoter can be accomplished, for example, by determining the ability of the EAAT2 promoter to bind to an EAAT2 promoter target molecule by one of the methods described above for determining direct binding. Determining the ability of the EAAT2 promoter to bind to an EAAT2 promoter target molecule can also be accomplished using a technology such as real-time Biomolecular Interaction Analysis (BIA). Sjolander, S. and Urbaniczky, C. (1991) Anal. Chem. 63:2338-2345 and Szabo et al. (1995) Curr. Opin. Struct. Biol. 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In yet another embodiment, the cell-free assay involves contacting an EAAT2 promoter or portion thereof with a known compound which binds the EAAT2 promoter (e.g., a component of the basal transcription machinery) to form an assay mixture, contacting the assay mixture with a test compound, and determining the ability of the test compound to interact with the EAAT2 promoter, wherein determining the ability of the test compound to interact with the EAAT2 promoter comprises determining the ability of the EAAT2 promoter to preferentially bind to or modulate the activity of an EAAT2 promoter target molecule.

In more than one embodiment of the above assay methods of the present invention, it may be desirable to immobilize either EAAT2 promoter or its target molecule to facilitate separation of complexed from uncomplexed forms of one or both of the molecules, as well as to accommodate automation of the assay. Binding of a test compound to an EAAT2 promoter, or interaction of an EAAT2 promoter with a substrate or target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/target fusion proteins can be adsorbed onto glutathione sepharose beads (Sigma Chemical, St. Louis, Mo.) or glutathione derivatized micrometer plates, which are then combined with the test compound or the test compound and either the non-adsorbed target protein or EAAT2 promoter, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of EAAT2 promoter binding or activity determined using standard techniques.

Other techniques for immobilizing proteins or nucleic acids on matrices can also be used in the screening assays of the invention. For example, either an EAAT2 promoter or an EAAT2 promoter substrate or target molecule can be immobilized utilizing conjugation of biotin and streptavidin. Biotinylated EAAT2 promoter, substrates, or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with EAAT2 promoter or target molecules but which do not interfere with binding of the EAAT2 promoter to its target molecule can be derivatized to the wells of the plate, and unbound target or EAAT2 promoter trapped in the wells by antibody conjugation. Methods for detecting such complexes, in addition to those described above for the GST-immobilized complexes, include immunodetection of complexes using antibodies reactive with the EAAT2 promoter or target molecule, as well as enzyme-linked assays which rely on detecting an enzymatic activity associated with the EAAT2 promoter or target molecule.

In yet another aspect of the invention, the EAAT2 promoter can be used as "bait" in a one-hybrid assay (see, e.g., BD Matchmaker One-Hybrid System (1995) Clontechniques X(3):2-4; BD Matchmaker Library Construction & Screening Kit (2000) Clontechniques XV(4):5-7; BD SMART technology overview (2002) Clontechniques XVII(1):22-28; Ausubel, F. M., et al. (1998 et seq.) Current Protocols in Molecular Biology Eds. Ausubel, F. M., et al., pp. 13.4.1-13.4.10) to identify proteins which bind to or interact with the EAAT2 promoter ("EAAT2 promoter-binding proteins" or "EAAT2 promoter-bp") and are involved in EAAT2 promoter activity. Such EAAT2 promoter-binding proteins are also likely to be involved in the regulation of transcription from the EAAT2 promoter.

In another aspect, the invention pertains to a combination of two or more of the assays described herein. For example, a modulating agent can be identified using a cell-based or a cell-free assay, and the ability of the agent to modulate the activity of an EAAT2 promoter can be confirmed in vivo, e.g., in an animal such as an animal model for a neurological disease.

This invention further pertains to novel agents identified by the above-described screening assays. Accordingly, it is within the scope of this invention to further use an agent identified as described herein in an appropriate animal model (e.g., an animal model for a neurological disease). For example, an agent identified as described herein (e.g., an EAAT2 promoter modulating agent or an EAAT2 promoter binding protein) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

IV. Methods of Treatment

In one embodiment, the present invention provides methods of treating neurological and psychiatric disorders which comprise administering a therapeutically effective amount of a pharmaceutical composition comprising an EAAT2 promoter modulator a subject (e.g., a mammal such as a human).

To modulate EAAT2 promoter activity, and thereby modulate EAAT2 gene expression, e.g., a compound disclosed herein or identified by the screening assays of the invention, can be administered to a cell or a subject. Administration of an EAAT2 promoter modulator to mammalian cells (including human cells) can modulate (e.g., up- or down-regulate EAAT2 mRNA and/or polypeptide expression, thereby up- or down-regulating glutamate transport into the cell. In such methods, the EAAT2 promoter can be administered to a mammal (including a human) by known procedures.

The preferred therapeutic methods of the invention (which include prophylactic treatment) in general comprise administration of a therapeutically effective amount of an EAAT2 promoter modulator to an animal in need thereof, including a mammal, particularly a human. Such treatment will be suitably administered to subjects, particularly humans, suffering from, having, susceptible to, or at risk for a neurological or psychiatric disorder. The EAAT2 promoter modulators of the invention may be also used in the treatment of any other disorders in which EAAT2 may be implicated.

For therapeutic applications, EAAT2 modulators of the invention may be suitably administered to a subject such as a mammal, particularly a human, alone or as part of a pharmaceutical composition, comprising the EAAT2 modulator together with one or more acceptable carriers thereof and optionally other therapeutic ingredients. The carrier(s) must be "acceptable" in the sense of being compatible with the other ingredients of the formulation and not deleterious to the recipient thereof.

The pharmaceutical compositions of the invention include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and in liposomes, and may be prepared by any methods well know in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Application of the subject therapeutics often will be local, so as to be administered at the site of interest. Various techniques can be used for providing the subject compositions at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way.

It will be appreciated that actual preferred amounts of a given EAAT2 modulator of the invention used in a given therapy will vary to the particular active compound being utilized, the particular compositions formulated, the mode of application, the particular site of administration, the patient's weight, general health, sex, etc., the particular indication being treated, etc. and other such factors that are recognized by those skilled in the art including the attendant physician or veterinarian. Optimal administration rates for a given protocol of administration can be readily determined by those skilled in the art using conventional dosage determination tests.

V. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining EAAT2 promoter activity, in the context of a biological sample (e.g., a sample of astroglial cells) to thereby determine whether an individual is afflicted with a disease or disorder, or is at risk of developing a disorder, associated with aberrant or unwanted EAAT2 expression or activity. The invention also provides for prognostic (or predictive) assays for determining whether an individual is at risk of developing a disorder associated with EAAT2 protein, nucleic acid expression, or activity. For example, mutations in the EAAT2 promoter can be assayed in a biological sample. Such assays can be used for prognostic or predictive purpose to thereby prophylactically treat an individual prior to the onset of a disorder characterized by or associated with EAAT2 protein, nucleic acid expression or activity.

Another aspect of the invention pertains to monitoring the influence of agents (e.g., drugs, compounds) on the expression or activity of EAAT2 in clinical trials.

These and other agents are described in further detail in the following sections.

1. Diagnostic Assays

An exemplary method for detecting the presence or absence of the EAAT2 promoter nucleic acid in a biological sample involves obtaining a biological sample from a test subject and contacting the biological sample with a compound or an agent capable of detecting EAAT2 promoter nucleic acid (e.g., genomic DNA) such that the presence of EAAT2 promoter nucleic acid is detected in the biological sample. A preferred agent for detecting EAAT2 promoter genomic DNA is a labeled nucleic acid probe capable of hybridizing to EAAT2 promoter genomic DNA. The nucleic acid probe can be, for example, a EAAT2 promoter nucleic acid of SEQ ID NO:1, 2, 3, or 4, or a portion thereof, such as an oligonucleotide of at least 15, 30, 50, 100, 250 or 500 nucleotides in length and sufficient to specifically hybridize under stringent conditions to EAAT2 promoter genomic DNA. Other suitable probes for use in the diagnostic assays of the invention are described herein.

The present invention also provides diagnostic assays for identifying the presence or absence of a genetic alteration characterized by aberrant modification or mutation of an EAAT2 promoter.

In another embodiment, the methods further involve obtaining a control biological sample from a control subject, contacting the control sample with a compound or agent capable of detecting EAAT2 promoter genomic DNA, such that the presence of EAAT2 promoter genomic DNA is detected in the biological sample, and comparing the presence of EAAT2 promoter genomic DNA in the control sample with the presence of EAAT2 promoter genomic DNA in the test sample.

The invention also encompasses kits for detecting she presence of the EAAT2 promoter in a biological sample. For example, the kit can comprise a labeled compound or agent capable of detecting EAAT2 promoter DNA in a biological sample; means for determining the amount and/or sequence of the EAAT2 promoter in the sample; and means for comparing the amount and/or sequence of the EAAT2 promoter in the sample with a standard. The compound or agent can be packaged in a suitable container. The kit can further comprise instructions for using the kit to detect EAAT2 promoter nucleic acid.

2. Prognostic Assays

The diagnostic methods described herein can furthermore be utilized to identify subjects having or at risk of developing a disease or disorder associated with aberrant or unwanted EAAT2 promoter activity. As used herein, the term "aberrant" includes a EAAT2 expression or activity which deviates from the wild type EAAT2 promoter activity. Aberrant activity includes increased or decreased activity, as well as activity which does not follow the wild type developmental pattern of expression or the subcellular pattern of expression. For example, aberrant EAAT2 promoter activity is intended to include the cases in which a mutation in the EAAT2 promoter causes the EAAT2 gene to be under-expressed or over-expressed and situations in which such mutations result in a non-functional EAAT2 protein or a protein which does not function in a wild-type fashion, e.g., a protein which does not interact with or transport a EAAT2 substrate (i.e., glutamate), or one which interacts with or transports a non-EAAT2 substrate. As used herein, the term "unwanted" includes an unwanted phenomenon involved in a biological response such as deregulated glutamate transport. For example, the term unwanted includes a EAAT2 expression or activity which is undesirable in a subject.

The assays described herein, such as the preceding diagnostic assays or the following assays, can be utilized to identify a subject having or at risk of developing a disorder associated with a misregulation in EAAT2 promoter activity, such as neurological or psychiatric disorder. Alternatively, the prognostic assays can be utilized to identify a subject having or at risk for developing a disorder associated with a misregulation in EAAT2 promoter activity, such as a neurological or psychiatric disorder. Thus, the present invention provides a method for identifying a disease or disorder associated with aberrant or unwanted EAAT2 promoter activity in which a test sample is obtained from a subject and EAAT2 promoter nucleic acid (e.g., genomic DNA) is detected (and/or sequenced), wherein the presence of an EAAT2 promoter modification or mutation is diagnostic for a subject having or at risk of developing a disease or disorder associated with aberrant or unwanted EAAT2 promoter activity. As used herein, a "test sample" refers to a biological sample obtained from a subject of interest. For example, a test sample can be a biological fluid, cell sample, or tissue, and is preferably astroglial cells.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted EAAT2 promoter activity. For example, such methods can be used to determine whether a subject can be effectively treated with an agent for a neurological or psychiatric disorder. Thus, the present invention provides methods for determining whether a subject can be effectively treated with an agent for a disorder associated with aberrant or unwanted EAAT2 promoter activity in which a test sample is obtained and EAAT2 promoter activity is detected.

The methods of the invention can also be used to detect genetic alterations in a EAAT2 promoter, thereby determining if a subject with the altered gene is at risk for a disorder characterized by misregulation in EAAT2 protein activity or nucleic acid expression, such as a neurological or psychiatric disorder. In preferred embodiments, the methods include detecting, in a sample of cells from the subject, the presence or absence of a genetic alteration characterized by at least one of an alteration affecting the integrity of the EAAT2 promoter. For example, such genetic alterations can be detected by ascertaining the existence of at least one of 1) a deletion of one or more nucleotides from an EAAT2 promoter; 2) an addition of one or more nucleotides to a EAAT2 promoter; 3) a substitution of one or more nucleotides of an EAAT2 promoter; 4) a chromosomal rearrangement of an EAAT2 promoter; 5) aberrant modification of a EAAT2 promoter, such as of the methylation pattern of the genomic DNA, and 6) allelic loss of an EAAT2 promoter. As described herein, there are a large number of assays known in the art which can be used for detecting alterations in an EAAT2 promoter. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in the EAAT2 promoter (see Abravaya et al. (1995) Nucleic Acids Res. 23:675-682). This method can include the steps of collecting a sample of cells from a subject, isolating nucleic acid (e.g., genomic DNA) from the cells of the sample, contacting the nucleic acid sample with one or more primers which specifically hybridize to a EAAT2 promoter under conditions such that hybridization and amplification of the EAAT2 promoter (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in the EAAT2 promoter can be identified by hybridizing a sample and control nucleic acids, e.g., DNA or RNA, to high density arrays containing hundreds or thousands of oligonucleotides probes (Cronin, M. T. et al. (1996) Hum. Mutat. 7:244-255; Kozal, M. J. et al. (1996) Nat. Med. 2:753-759). For example, genetic mutations in the EAAT2 promoter can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the EAAT2 promoter and detect mutations by comparing the sequence of the sample EAAT2 promoter with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays (Naeve, C. W. (1995) Biotechniques 19:448), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the EAAT2 promoter include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type EAAT2 promoter sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397; Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in EAAT2 cDNAs obtained from samples of cells. For example, the mutY enzyme of $E.\ coli$ cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a EAAT2 promoter sequence, e.g., a wild-type EAAT2 promoter sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in the EAAT2 promoter. For example, single strand conformation polymorphism (SSCP) may be used to detect differences in electrophoretic mobility between mutant and wild type nucleic acids (Orita et al. (1989) Proc. Natl. Acad. Sci. USA 86:2766, see also Cotton (1993) Mutat. Res. 285:125-144; and Hayashi (1992) Genet. Anal. Tech. Appl. 9:73-79). Single-stranded DNA fragments of sample and control EAAT2 promoter nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci. USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an EAAT2 promoter.

Furthermore, any cell type or tissue in which EAAT2 is expressed (e.g., astroglial cells) may be utilized in the prognostic assays described herein.

3. Monitoring of Effects During Clinical Trials

Monitoring the influence of agents (e.g., drugs) on the activity of the EAAT2 promoter can be applied not only in basic drug screening, but also in clinical trials. For example, the effectiveness of an agent determined by a screening assay as described herein to increase EAAT2 promoter activity, can be monitored in clinical trials of subjects exhibiting decreased EAAT2 promoter activity. Alternatively, the effectiveness of an agent determined by a screening assay to decrease EAAT2 promoter activity, can be monitored in clinical trials of subjects exhibiting increased EAAT2 promoter activity. In such clinical trials, the expression or activity of a EAAT2 promoter, and preferably, other genes that have been implicated in, for example, a neurological or psychiatric disorder can be used as a "read out" or markers of the phenotype of a particular cell.

For example, and not by way of limitation, genes, including EAAT2, that are modulated in cells by treatment with an agent (e.g., compound, drug or small molecule) which modulates EAAT2 promoter activity (e.g., identified in a screening assay as described herein) can be identified. Thus, to study the effect of agents on neurological or psychiatric disorders, for example, in a clinical trial, cells can be isolated and RNA prepared and analyzed for the levels of expression of EAAT2 and other genes implicated in the disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of EAAT2 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a preadministration sample from a subject prior to administration of the agent; (ii) detecting the level of expression of a EAAT2 protein, mRNA, or genomic DNA in the preadministration sample; (iii) obtaining one or more post-administration samples from the subject; (iv) detecting the level of expression or activity of the EAAT2 protein, mRNA, or genomic DNA in the post-administration samples; (v) comparing the level of expression or activity of the EAAT2 protein, mRNA, or genomic DNA in the pre-administration sample with the EAAT2 protein, mRNA, or genomic DNA in the post administration sample or samples; and (vi) altering the administration of the agent to the subject accordingly. For example, increased administration of the agent may be desirable to increase the expression or activity of EAAT2 to higher levels than detected, i.e., to increase the effectiveness of the agent. Alternatively, decreased administration of the agent may be desirable to decrease expression or activity of EAAT2 to lower levels than detected, i.e., to decrease the effectiveness of the agent. According to such an embodiment, EAAT2 expression or activity may be used as an indicator of the effectiveness of an agent, even in the absence of an observable phenotypic response.

This invention is further illustrated by the following examples which should not be construed as limiting. The contents of all references, patents and published patent applications cited throughout this application, as well as the sequence listing and the figures, are incorporated herein by reference.

EXAMPLES

Example 1

Identification and Cloning of the Eaat2 Promoter

A genomic DNA PAC clone known from a BLAST search to contain the 5' end of the EAAT2 gene was obtained from the Sanger Institute, Cambridge, United Kingdom. The clone was grown up according to the supplier's instructions, and DNA was isolated and digested with EcoRI. Fragments were resolved on a 0.8% agarose gel and transferred to a nitrocellulose membrane. The blot was probed with a random-primed 130 bp PCR product containing EAAT2 exon 1. An 8 kb EcoRI fragment generated a positive hybridization signal, and this fragment was subsequently subcloned into a TA-vector. Sequence data revealed that this fragment did contain exon 1 and additional sequence upstream of exon 1 (2.8 kb of the 8 kb fragment), which was obtained and analyzed for promoter motifs.

Example 2

Analysis of the EAAT2 Promoter

The sequence of the EAAT2 promoter and flanking DNA is shown in FIGS. 1A-1B and set forth as SEQ ID NO:1. This sequence was analyzed using the PROSCAN Version 1.7 suite of software programs developed by Dr. Dan Prestridge (Prestridge, D. S. (1995) *J. Mol. Biol.* 249: 923-32), which are designed to find putative eukaryotic Pol II promoter sequences in primary sequence data. Potential promoter elements identified using this analysis include CCAAT boxes, SpI binding sites (GGGGCGGGG or CCCCGCCCC), E-box motifs (CACCTG, CAYGTG or CANNTG), binding sites for elements from the GATA family of transcription factors (motifs that can affect kidney tissue expression), NF-κB, and binding sites for WT1 (GNGGGNGNG). Nucleotide repeat regions, poly(dA:dT) and poly(dG:dT), that are thought to affect transcription through conformational changes in the DNA structure were also found in the flanking sequence. Notably, cyclic AMP response elements (CREB binding domains) were also identified in this first 2.8 kb fragment. As described elsewhere herein, GLT-1/EAAT2 is known to be upregulated by cyclic AMP, which typically activates transcription thru cyclic AMP response elements (CREB). Several possible CREB promoter motifs were also found within the EAAT2 promoter. A schematic representation of the EAAT2 promoter region showing the identified promoter elements is shown in FIG. 2. The full results of the PROSCAN analysis are set forth below in Tables I-VI.

TABLE I

Promoter region predicted on forward strand in 2059 to 2309
Promoter Score: 60.44 (Promoter Cutoff = 53.000000)
Significant Signals:

| Name | TFD # | Strand | Location | Weight |
|------|-------|--------|----------|--------|
| GCF  | S01964 | +     | 2126     | 2.361000 |
| AP-2 | S00346 | +     | 2129     | 1.355000 |
| Sp1  | S00802 | +     | 2129     | 3.292000 |
| GCF  | S01964 | −     | 2132     | 2.284000 |

TABLE I-continued

Promoter region predicted on forward strand in 2059 to 2309
Promoter Score: 60.44 (Promoter Cutoff = 53.000000)
Significant Signals:

| Name | TFD # | Strand | Location | Weight |
|---|---|---|---|---|
| AP-2 | S01936 | + | 2132 | 1.108000 |
| Sp1 | S00978 | − | 2134 | 3.361000 |
| Sp1 | S00333 | − | 2135 | 3.442000 |
| (Sp1) | S00857 | − | 2136 | 4.876000 |
| JCV_repeated_sequenc | S01193 | + | 2171 | 1.427000 |
| Sp1 | S00801 | + | 2187 | 2.755000 |
| Sp1 | S00781 | − | 2192 | 2.772000 |
| UCE.2 | S00437 | − | 2207 | 1.216000 |
| UCE.2 | S00437 | + | 2241 | 1.278000 |
| UCE.2 | S00437 | − | 2285 | 1.216000 |
| AP-2 | S01936 | + | 2295 | 1.108000 |
| EARLY-SEQ1 | S01081 | + | 2295 | 6.322000 |
| (Sp1) | S01187 | + | 2295 | 8.117000 |
| Sp1 | S00801 | + | 2296 | 2.755000 |
| AP-2 | S00346 | + | 2297 | 1.355000 |
| Sp1 | S00802 | + | 2297 | 3.292000 |
| Sp1 | S00781 | − | 2301 | 2.772000 |
| SP1 | S00978 | − | 2302 | 3.361000 |
| JCV_repeated-sequenc | S01193 | − | 2302 | 1.658000 |

TABLE II

Promoter region predicted on forward strand in 3187 to 3437
Promoter Score: 54.08 (Promoter Cutoff = 53.000000)
Significant Signals:

| Name | TFD # | Strand | Location | Weight |
|---|---|---|---|---|
| Sp1 | S00801 | + | 3187 | 2.755000 |
| AP-2 | S00346 | + | 3188 | 1.355000 |
| Sp1 | S00781 | − | 3192 | 2.772000 |
| AP-2 | S01936 | + | 3202 | 1.108000 |
| AP-2 | S00180 | + | 3204 | 1.863000 |
| Sp1 | S00978 | + | 3208 | 3.013000 |
| Sp1 | S00977 | + | 3208 | 7.086000 |
| JCV_repeated_sequenc | S01193 | + | 3208 | 1.427000 |
| AP-2 | S00346 | − | 3213 | 1.672000 |
| Sp1 | S00802 | − | 3213 | 3.061000 |
| EARLY-SEQ1 | S01081 | − | 3215 | 5.795000 |
| AP-2 | S01936 | − | 3218 | 1.091000 |
| GCF | S01964 | + | 3229 | 2.361000 |
| Sp1 | S00781 | + | 3312 | 3.191000 |
| JCV_repeated_sequenc | S01193 | + | 3315 | 1.427000 |
| Sp1 | S00801 | − | 3317 | 3.119000 |
| Sp1 | S00978 | + | 3323 | 3.013000 |
| Sp1 | S00802 | − | 3328 | 3.061000 |
| UCE.2 | S00437 | + | 3357 | 1.278000 |
| UCE.2 | S00437 | − | 3360 | 1.216000 |
| AP-2 | S01936 | + | 3375 | 1.108000 |
| T-Ag | S00974 | + | 3430 | 1.086000 |
| (Sp1) | S01027 | − | 3436 | 2.233000 |

TABLE III

Promoter region predicted on forward strand in 3820 to 4070
Promoter Score: 94.21 (Promoter Cutoff = 53.000000)
Significant Signals:

| Name | TFD # | Strand | Location | Weight |
|---|---|---|---|---|
| GCF | S01964 | + | 3820 | 2.361000 |
| TTR_inverted_repeat | S01112 | − | 3827 | 3.442000 |
| AP-2 | S01936 | + | 3828 | 1.108000 |
| AP-2 | S00180 | + | 3828 | 1.863000 |
| GCF | S01964 | − | 3828 | 2.284000 |
| Sp1 | S00781 | + | 3840 | 3.191000 |
| Sp1 | S00801 | − | 3845 | 3.119000 |
| T-Ag | S00974 | + | 3893 | 1.086000 |

TABLE III-continued

Promoter region predicted on forward strand in 3820 to 4070
Promoter Score: 94.21 (Promoter Cutoff = 53.000000)
Significant Signals:

| Name | TFD # | Strand | Location | Weight |
|---|---|---|---|---|
| Sp1 | S00979 | + | 3893 | 6.023000 |
| Sp1 | S00645 | + | 3893 | 12.906000 |
| Sp1 | S00064 | + | 3893 | 10.681000 |
| Sp1 | S01542 | + | 3893 | 6.661000 |
| JCV_repeated_sequenc | S01193 | + | 3894 | 1.427000 |
| Sp1 | S00978 | + | 3894 | 3.013000 |
| AP-2 | S01936 | − | 3895 | 1.091000 |
| GCF | S01964 | + | 3896 | 2.361000 |
| Sp1 | S00802 | − | 3899 | 3.061000 |
| EARLY-SEQ1 | S01081 | − | 3901 | 5.795000 |
| (Sp1) | S01187 | − | 3901 | 6.819000 |
| APRT-mouse_US | S00216 | − | 3902 | 7.604000 |
| UCE.2 | S00437 | − | 3922 | 1.216000 |
| GCF | S01964 | − | 3967 | 2.284000 |
| NF-kB | S01644 | − | 4004 | 50.000000 |
| JCV_repeated_sequenc | S01193 | + | 4022 | 1.427000 |
| Sp1 | S00781 | + | 4052 | 3.191000 |
| E2F | S01247 | + | 4053 | 25.816999 |
| E2F | S01242 | + | 4053 | 17.211000 |
| Sp1 | S00801 | − | 4057 | 3.119000 |
| E2F | S01952 | − | 4061 | 6.454000 |

TABLE IV

Promoter region predicted on reverse strand in 3565 to 3315 Promoter Score: 70.71
Promoter Cutoff = 53.000000) TATA found at 3350, Est.TSS = 3318
Significant Signals:

| Name | Strand | Location | Weight |
|---|---|---|---|
| Sp1 | − | 3561 | 2.755000 |
| GCF | + | 3557 | 2.284000 |
| Sp1 | + | 3556 | 2.772000 |
| T-Ag | − | 3525 | 1.086000 |
| c-fos.5 | − | 3522 | 1.912000 |
| AP-2 | − | 3513 | 1.108000 |
| MLTF | − | 3506 | 1.157000 |
| AP-2 | + | 3375 | 1.091000 |
| UCE.2 | − | 3360 | 1.278000 |
| UCE.2 | + | 3357 | 1.216000 |
| Sp1 | − | 3329 | 2.755000 |
| Sp1 | − | 3328 | 3.292000 |
| Sp1 | + | 3324 | 2.772000 |
| Sp1 | + | 3323 | 3.361000 |
| JCV_repeated_sequenc | + | 3315 | 1.658000 |

TABLE V

Promoter region predicted-on reverse strand in 3065 to 2815
Promoter Score: 77.12 (Promoter Cutoff = 53.000000)
Significant Signals:

| Name | Strand | Location | Weight |
|---|---|---|---|
| TTR_inverted_repeat | + | 3055 | 3.442000 |
| Sp1 | − | 3051 | 3.191000 |
| Sp1 | + | 3046 | 3.119000 |
| GCF | − | 2991 | 2.361000 |
| AP-2 | + | 2981 | 1.091000 |
| AP-2 | + | 2980 | 1.064000 |
| AP-2 | + | 2979 | 1.672000 |
| AP-2 | + | 2979 | 1.721000 |
| UCE.2 | − | 2969 | 1.278000 |
| UCE.2 | + | 2941 | 1.216000 |
| JCV_repeated_sequenc | − | 2939 | 1.427000 |

TABLE V-continued

Promoter region predicted-on reverse strand in 3065 to 2815
Promoter Score: 77.12 (Promoter Cutoff = 53.000000)
Significant Signals:

| Name | Strand | Location | Weight |
|---|---|---|---|
| APRT-mouse US | − | 2919 | 6.003000 |
| AP-2 | − | 2918 | 1.108000 |
| Sp1 | − | 2917 | 2.755000 |
| GCF | + | 2913 | 2.284000 |
| Sp1 | + | 2912 | 2.772000 |
| GCF | − | 2854 | 2.361000 |
| Sp1 | − | 2823 | 3.292000 |
| AP-2 | − | 2823 | 1.355000 |
| AP-2 | − | 2820 | 1.108000 |
| S Sp1 | − | 2819 | 9.386000 |
| EARLY-SEQ1 | − | 2818 | 6.322000 |
| (Sp1) | − | 2818 | 8.117000 |
| Sp1 | + | 2818 | 3.361000 |
| Sp1 | − | 2817 | 2.755000 |
| (Sp1) | + | 2816 | 4.876000 |

TABLE VI

Promoter region predicted on reverse strand in 2445 to 2195
Promoter Score: 53.54 (Promoter Cutoff = 53.000000)
Significant Signals:

| Name | Strand | Location | Weight |
|---|---|---|---|
| GCF | − | 2401 | 2.361000 |
| UCE.2 | + | 2396 | 1.216000 |
| AP-2 | − | 2382 | 1.355000 |
| AP-2 | − | 2381 | 1.108000 |
| Sp1 | − | 2379 | 2.755000 |
| JCV_repeated_sequenc | + | 2379 | 1.658000 |
| H4TF1 | + | 2377 | 2.099000 |
| Sp1 | + | 2374 | 2.772000 |
| (Sp1) | − | 2311 | 4.589000 |
| T-Ag | − | 2310 | 1.086000 |
| Sp1 | − | 2309 | 3.013000 |
| AP-2 | + | 2308 | 1.091000 |
| Sp1 | − | 2305 | 3.191000 |
| Sp1 | + | 2304 | 3.061000 |
| JCV_repeated_sequenc | − | 2302 | 1.427000 |
| Sp1 | + | 2300 | 3.119000 |
| AP-2 | + | 2297 | 1.672000 |
| (Sp1) | + | 2295 | 6.819000 |
| EARLY-SEQ1 | + | 2295 | 5.795000 |
| UCE.2 | − | 2285 | 1.278000 |
| UCE.2 | + | 2241 | 1.216000 |
| UCE.2 | − | 2207 | 1.278000 |
| SDR_RS | − | 2203 | 1.554000 |
| AP-2 | + | 2198 | 1.091000 |

Figure 3A:
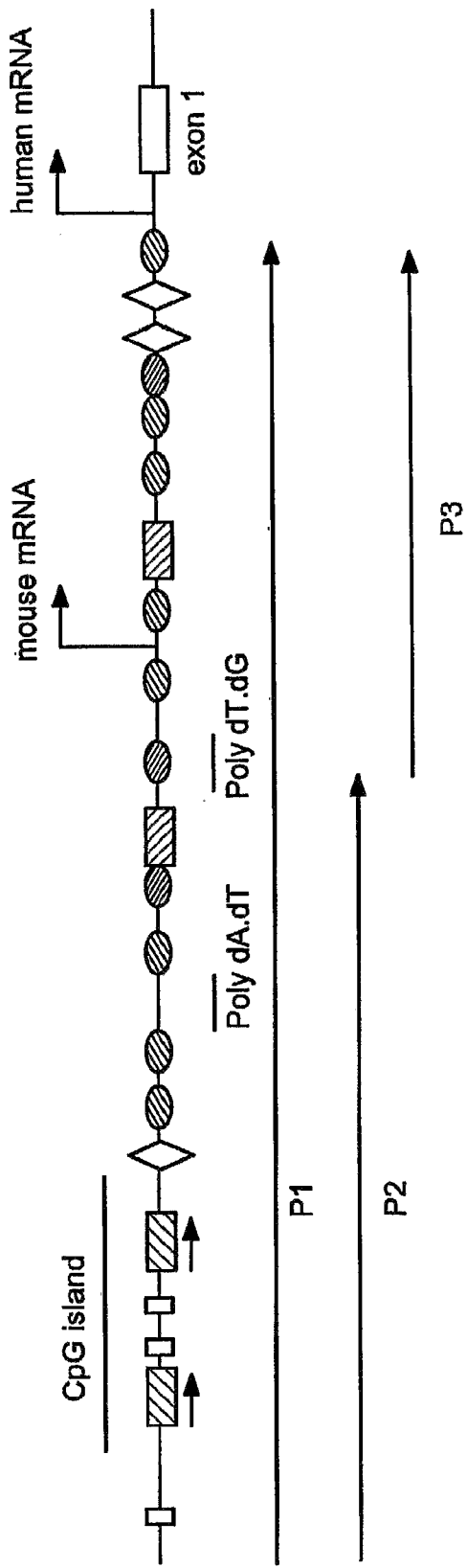
FIG. 3 depicts the results of a luciferase reporter activity assay using the P1, P2, and P3 EAAT2 promoter regions.
Figure 3B:
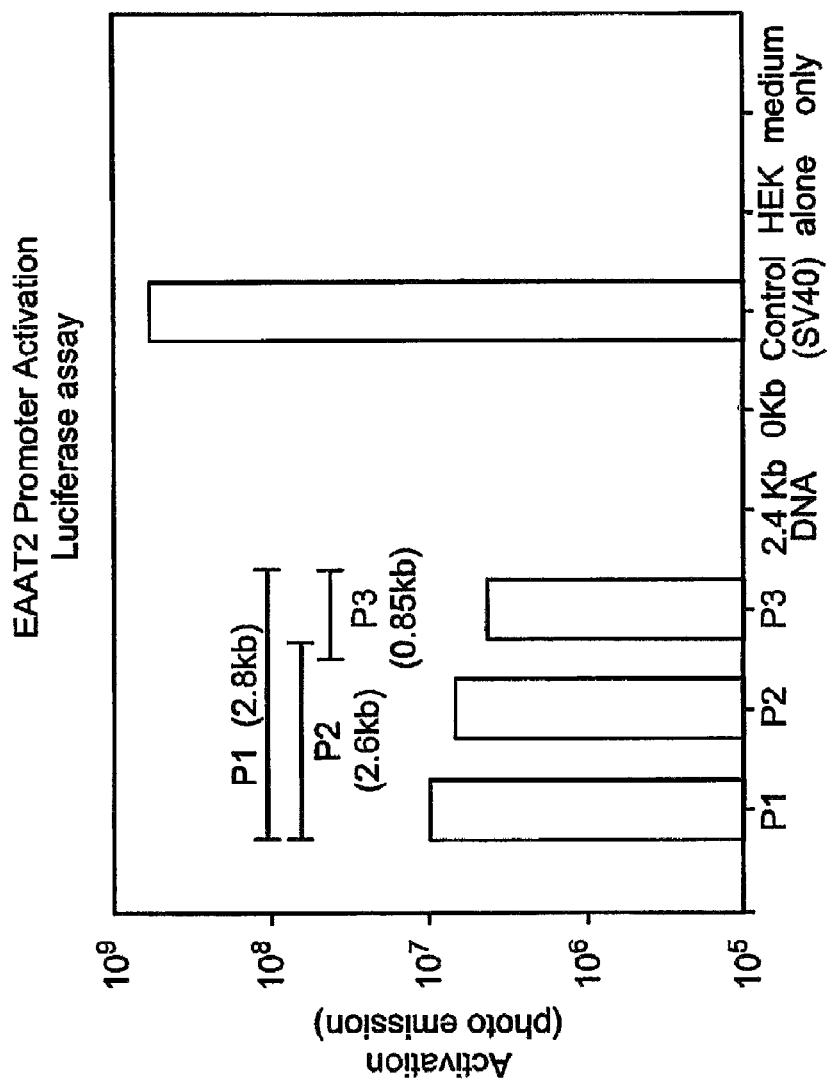

Three regions derived from different restriction enzyme digests of the 5' EAAT2 flanking region of the promoter (P1, P2, P3) were identified: an ~2.8 kb KpnI-NcoI fragment (P1), an ~2.5 kb KpnI-SalI fragment (P2) and an ~0.86 kb SmaI-SalI fragment (P3). The P1, P2, and P3 fragments were amplified by PCR and cloned into a promoterless luciferase reporter vector (pGL3, Promega, Madison, Wis.). The constructs were transiently transfected into various cell lines, including HEK 293T cells, COS7 cells, and C6 glioma cells, and luciferase activity was measured. The highest level of expression was obtained from COS7 cells. To control for transfection efficiency, luciferase activities were normalized with Renilla luciferase activity or β-galactosidase activity (FIG. 3). In preliminary studies, the 2.8 upstream EAAT2 promoter fragment was operatively linked with the EAAT2 cDNA. In transient transfection, EAAT2 protein was detected in COS-7 cells containing this construct.

Example 3

Production of EAAT2 Transgenic Mice

Two independent lines of transgenic mice based on the EAAT2 promoter were created. The first line contained the P1 fragment linked to enhanced green fluorescent protein (eGFP). This DNA construct was subcloned into a Stealth-Gene vector (Tosk, Inc., Santa Cruz, Calif.) that contains a modified P transposable element (see U.S. Pat. No. 6,291,243). The vector was injected into adult mice (C57), and approximately 40% of all cells, including the reproductive cells, have inserted, active cDNA. The mice were mated with wild-type mice to produce a colony of "founders". These mice have been mated and have confirmed transgenic expression.

Figure 5:
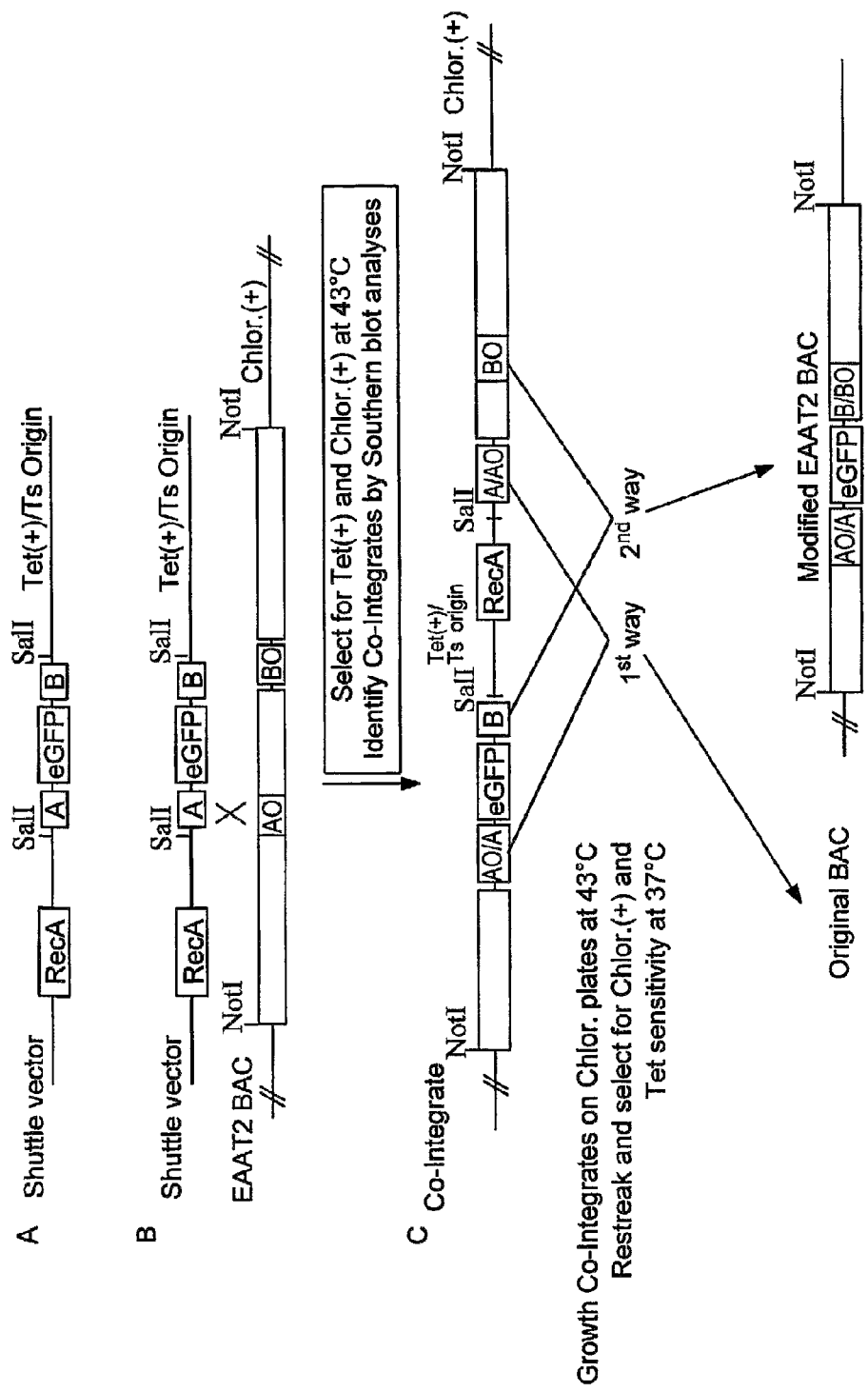
FIG. 5 depicts the strategy to be used in the generation of EAAT2 promoter BAC transgenic mice.

A second line of transgenic mice are created using a BAC clone. The BAC transgenic approach is described in Yang, X. W. et al. (1997) Nat. Biotechnol. 15(9):859-65, incorporated herein by reference. The BAC clone shown in FIG. 4 was chosen to include approximately 100 kb upstream of the EAAT2/GLT-1 coding sequence, as well as at least 120 kb that comprises the estimated EAAT2 gene. With targeted modification of a BAC clone containing a specific gene of interest (e.g., EAAT2), and subsequent germline transmission in transgenic mice, reporter cassettes may be used to study expression driven by the gene's promoter without specifically identifying promoter regulatory elements. One specific strategy that has been developed for manipulation of BAC DNA uses homologous recombination, mediated via the RecA protein, between a RecA+ shuttle vector containing the modification cassette and BAC DNA in RecA− host bacteria as described in Yang et al. (1997) supra. An eGFP reporter gene will be inserted at the initiation of the coding sequence using the shuttle vector. A schematic showing the protocol for generating the mice is shown in FIG. 5.

The invention has been described in detail with reference to preferred embodiments thereof. However, it will be appreciated that those skilled in the art, upon consideration of this disclosure, may make modification and improvements within the spirit and scope of the invention as set forth in the following claims.

What is claimed:

1. An isolated nucleic acid molecule consisting of the nucleic acid of SEQ ID NO: 1, SEQ ID NO: 2, SEQ ID NO: 3, or SEQ ID NO: 4, or a fragment thereof, wherein said fragment has EAAT2 promoter activity and comprises a promoter element selected from the group consisting of: a CAATT box, an SP1 binding site, an E-box motif, a GATA family transcription factor binding site, an NF-κB binding site, a WT1 binding site, a poly(dG:dT) repeat region, or a CREB binding site.

2. A vector comprising the nucleic acid molecule of claim 1.

3. The vector of claim 2, which is an expression vector.

4. An isolated host cell transfected with the expression vector of claim 3.

5. An isolated nucleic acid molecule comprising the nucleic acid molecule of claim 1 and a cDNA molecule operably linked to said nucleic acid molecule.

6. The nucleic acid molecule of claim 5, wherein the cDNA molecule comprises the EAAT2 cDNA sequence.

7. The nucleic acid molecule of claim 5, wherein the cDNA molecule comprises a reporter gene.

8. The nucleic molecule of claim 7, wherein the reporter gene is selected from the group consisting of luciferase, .beta.-galactosidase, chloramphenicol acetyl transferase, and a fluorescent protein.

9. The nucleic acid molecule of claim 8, wherein the luciferase is selected from the group consisting of firefly luciferase and Renilla luciferase.

10. The nucleic acid molecule of claim 8, wherein the fluorescent protein is selected from the group consisting of green fluorescent protein, red fluorescent protein, yellow fluorescent protein, blue fluorescent protein, and cyan fluorescent protein.

11. A vector comprising the nucleic acid molecule of claim 5.

12. The vector of claim 11, which is an expression vector.

13. An isolated host cell transfected with the expression vector of claim 12.

14. A method of producing an mRNA molecuie or a polypeptide comprising culturing the host cell of claim 13 in an appropriate culture medium to, thereby, produce the mRNA molecule or the polypeptide, wherein said mRNA molecule or polypeptide is encoded by the cDNA molecule.

15. The method of claim 14, wherein the cDNA molecule comprises the EAAT2 cDNA sequence.

16. The method of claim 14, wherein the cDNA molecule comprises a reporter gene.

17. The method of claim 16, wherein the reporter gene is selected from the group consisting of luciferase, .beta.-galactosidase, chloramphenicol acetyl transferase, and a fluorescent protein.

18. The method of claim 17, wherein the luciferase is selected from the group consisting of firefly luciferase and Renilla luciferase.

* * * * *